(12) United States Patent
Walsh et al.

(10) Patent No.: US 9,561,544 B2
(45) Date of Patent: Feb. 7, 2017

(54) METHODS AND DEVICES FOR SAFELY PENETRATING MATERIALS

(75) Inventors: Conor James Walsh, Dublin (IE); Ajith Thomas, Brookline, MA (US); Samuel Benjamin Kesner, Arlington, MA (US); Hao Pei, Maanshan (CN); Kechao Xiao, Guangzhou (CN); Paul Loschak, Sunrise, FL (US); Kevin C. Galloway, Somerville, MA (US)

(73) Assignees: BETH ISRAEL DEACONESS MEDICAL CENTER, INC., Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 252 days.

(21) Appl. No.: 14/240,878

(22) PCT Filed: Aug. 27, 2012

(86) PCT No.: PCT/US2012/052470
§ 371 (c)(1),
(2), (4) Date: Apr. 24, 2014

(87) PCT Pub. No.: WO2013/029039
PCT Pub. Date: Feb. 28, 2013

(65) Prior Publication Data
US 2014/0239600 A1  Aug. 28, 2014

Related U.S. Application Data

(60) Provisional application No. 61/527,585, filed on Aug. 25, 2011.

(51) Int. Cl.
| A61B 17/16 | (2006.01) |
| B23B 31/117 | (2006.01) |
| B23B 41/00 | (2006.01) |

(52) U.S. Cl.
CPC ......... *B23B 31/117* (2013.01); *A61B 17/1624* (2013.01); *A61B 17/1626* (2013.01);
(Continued)

(58) Field of Classification Search
CPC .. Y10T 408/665; Y10T 408/73; Y10T 408/75; Y10T 408/551; Y10T 408/18; Y10T 408/20; Y10T 408/15; A61B 17/16; A61B 17/1631; A61B 17/1695
See application file for complete search history.

(56) References Cited

U.S. PATENT DOCUMENTS 1,346,295 A * 7/1920 Burger .................... B23G 1/46
                                                    279/9.1
1,711,427 A * 4/1929 Sauveur ................. B23B 31/38
                                                    279/103
(Continued)

FOREIGN PATENT DOCUMENTS

| EP | 0873720 A1 | 10/1998 |
| JP | 57201114 A * | 12/1982 |

(Continued)

OTHER PUBLICATIONS

Machine translation of SU 1808508, printed Apr. 2016.*
(Continued)

*Primary Examiner* — Daniel Howell
(74) *Attorney, Agent, or Firm* — Nixon Peabody LLP; David S. Resnick; David F. Crosby

(57) ABSTRACT

The present invention is directed to a bi-stable coupling for controlling the depth of a tool insertion, such as drilling, and similar processes. The bi-stable coupling can be used to penetrate (e.g., drill or push) through a material layer of unknown thickness without plunging the tool into the adjacent layer. In accordance with the invention, in a first state, force is applied to the tool to initiate penetration and a
(Continued)

reactive force maintains the device in the first state during penetration and when tool penetrates the material, the reactive force is diminished enabling the device to transition to a second state in which the tool becomes retracted. In medical applications, the invention allows for drilling through bone of unknown thickness without plunging into the adjacent soft tissue.

17 Claims, 20 Drawing Sheets

(52) U.S. Cl.
CPC .......... *A61B 17/1695* (2013.01); *B23B 41/00* (2013.01); *A61B 90/03* (2016.02); *Y10T 279/33* (2015.01); *Y10T 408/20* (2015.01); *Y10T 408/551* (2015.01); *Y10T 408/665* (2015.01)

(56) References Cited

U.S. PATENT DOCUMENTS

| | | | |
|---|---|---|---|
| 2,842,131 A | 7/1958 | Smith | |
| 4,273,117 A | 6/1981 | Neuhaeuser | |
| 4,362,161 A | 12/1982 | Reimels et al. | |
| 4,456,010 A | 6/1984 | Reimels et al. | |
| 4,555,203 A * | 11/1985 | Takahashi | B23B 45/00 408/119 |
| 4,600,006 A | 7/1986 | Baker | |
| 4,699,550 A | 10/1987 | Baker | |
| 4,803,982 A | 2/1989 | Baker | |
| 4,884,571 A | 12/1989 | Baker | |
| 5,135,532 A | 8/1992 | Baker | |
| 5,382,250 A | 1/1995 | Kraus | |
| 5,876,405 A | 3/1999 | Del Rio et al. | |
| 5,993,453 A | 11/1999 | Bullara et al. | |
| 6,716,215 B1 | 4/2004 | David et al. | |
| 6,863,136 B2 | 3/2005 | Bar-Cohen et al. | |
| 6,968,910 B2 | 11/2005 | Bar-Cohen et al. | |
| D596,743 S | 7/2009 | Agbodoe et al. | |
| 7,740,088 B1 | 6/2010 | Bar-Cohen et al. | |
| 7,824,247 B1 | 11/2010 | Bar-Cohen et al. | |
| 8,480,682 B2 | 7/2013 | Howlett et al. | |
| 2011/0054483 A1 | 3/2011 | Howlett et al. | |

FOREIGN PATENT DOCUMENTS

| | | |
|---|---|---|
| JP | 58010416 A * | 1/1983 |
| RU | 1808508 A1 * | 4/1993 |
| SU | 971586 A * | 11/1982 |

OTHER PUBLICATIONS

"Acra-Cut Smart Drill", Acra-Cut, 2003, http://www.acracut.com/images/pdf/smartdrill.pdf.

Agamanolis, Neuropathology online course, Northeastern Ohio Universities College of Medicine (NEOUCOM) http://neuropathology-web.org/chapter4/chapter4aSubduralepidural.html.

Caird et al., "'Plunging' during burr hole craniostomy: a persistent problem amongst neurosurgeons in Britain and Ireland", Br. J. Neurosurg. 17(6):509-512 (2003).

Faul et al. "Traumatic Brain Injury in the United States: Emergency Department Visits, Hospitalizations and Deaths 2002-2006" Atlanta, GA: Centers for Disease Control and Prevention, National Center for Injury Prevention and Control (2010).

Gelabert-Gonzalez et al., "The Camino intracranial pressure device in clinical practice. Assessment in a 1000 cases", Acta Neurochir. 148(4):435-441 (2006).

Glauser et al., "Conception of a robot dedicated to neurosurgical operations" Fifth International Conference on Advanced Robotics. Robots in Unstructured Environment 1:899-904 (1991).

Lynnerup, "Cranial thickness in relation to age, sex and general body build in a Danish forensic sample", Forensic Sci. Int. 117:45-51 (2001).

Stein et al., "Relationship of aggressive monitoring and treatment to improved outcomes in severe traumatic brain injury", J. Neurosurg. 112:1105-1112 (2010).

Tsai et al., "Bone drilling haptic interaction for orthopedic surgical simulator", Computers in Biology and Medicine 37:1709-1718 (2007).

* cited by examiner

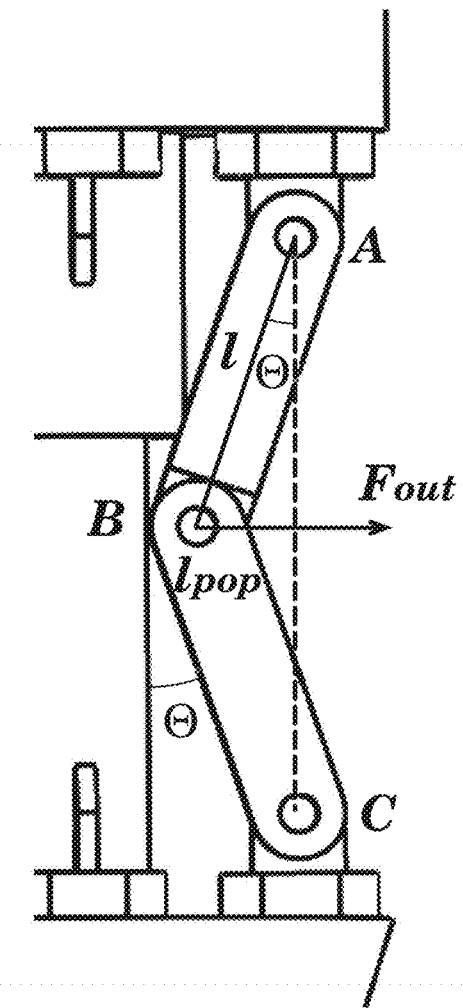
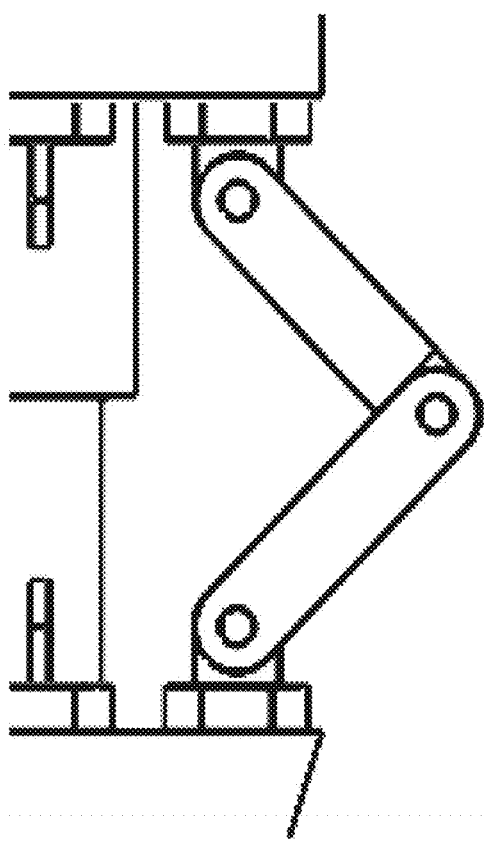
*FIG. 6A*  *FIG. 6B*

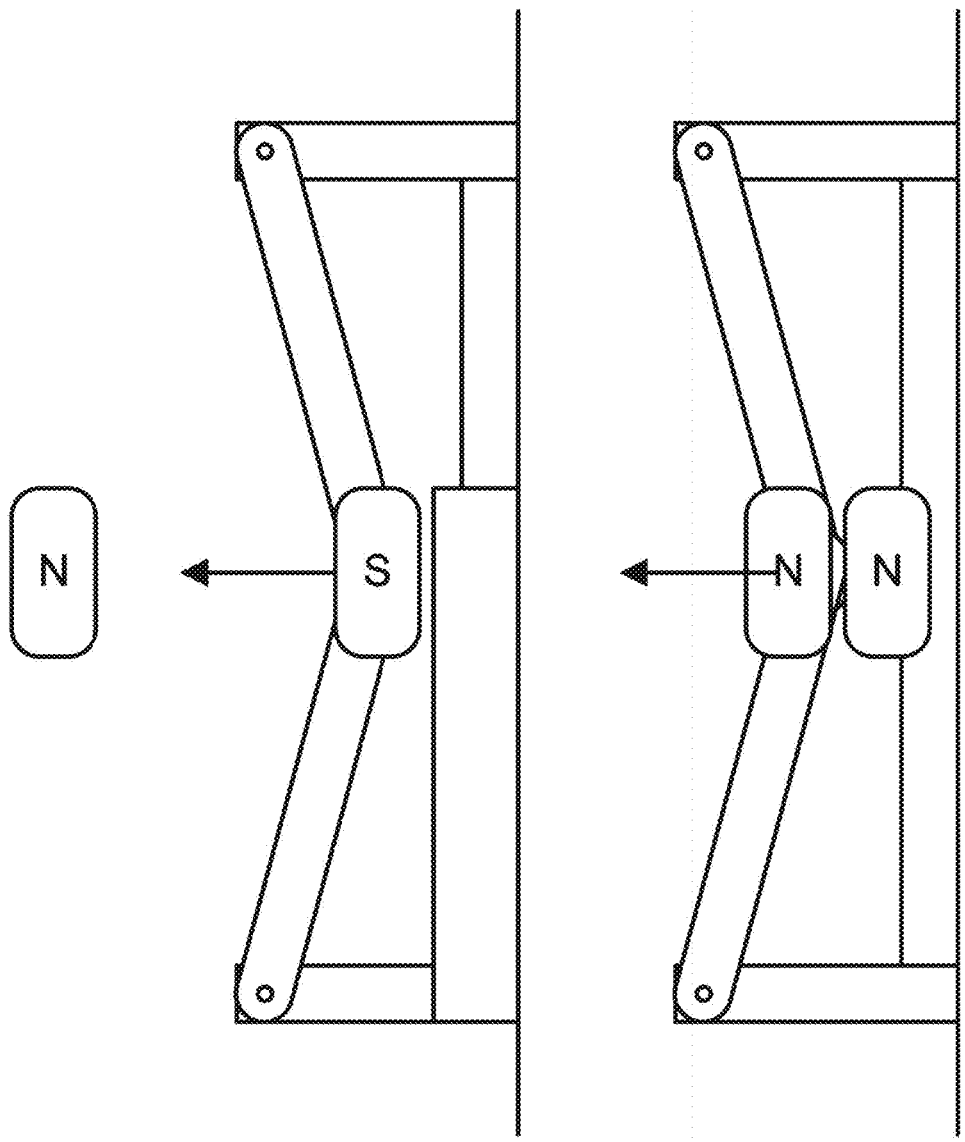
*FIG. 12A*  *FIG. 12B*

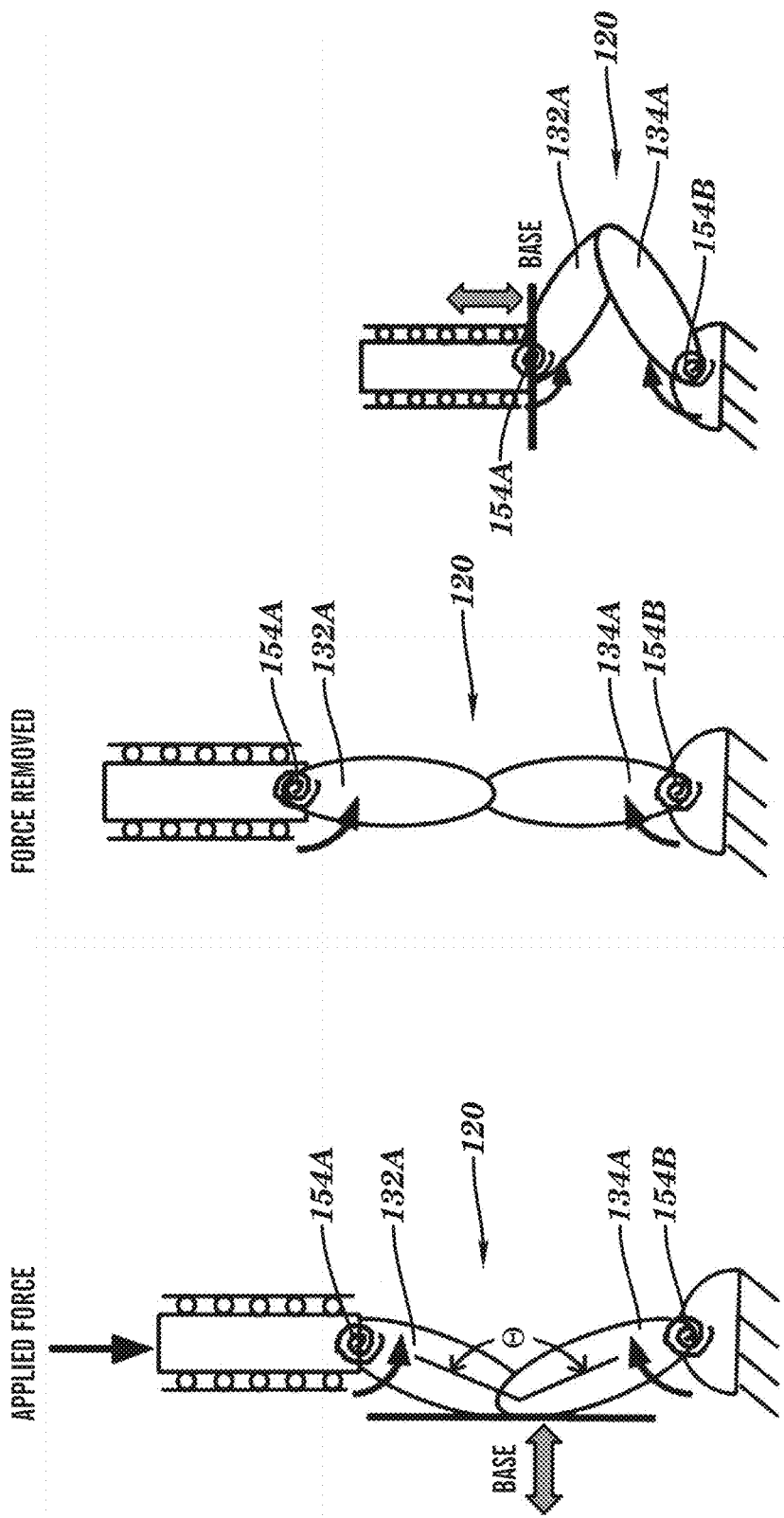

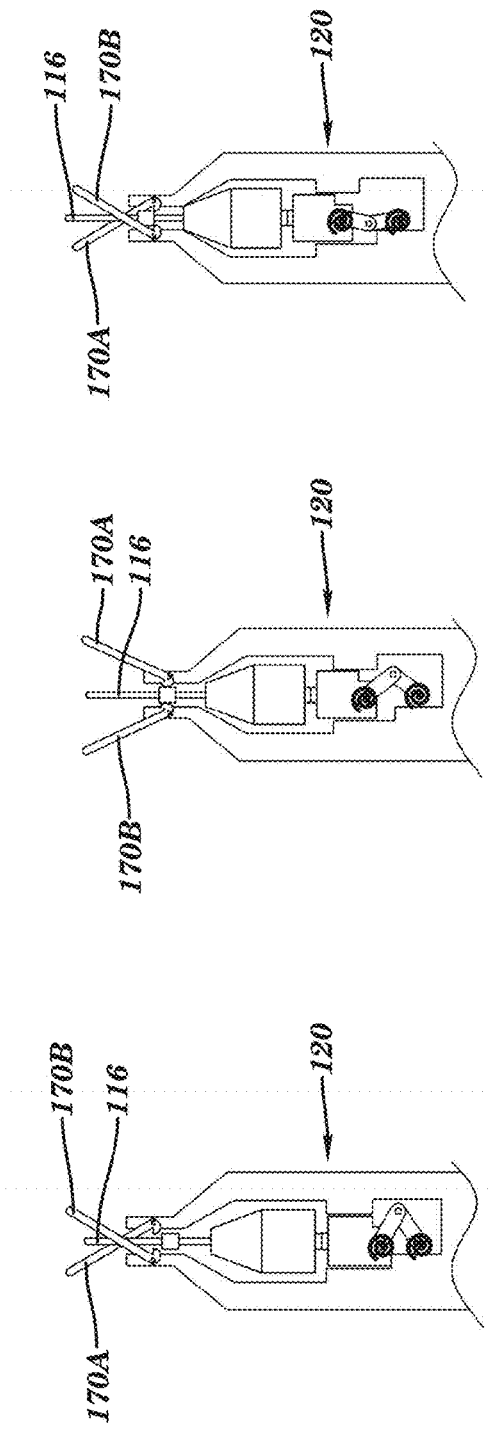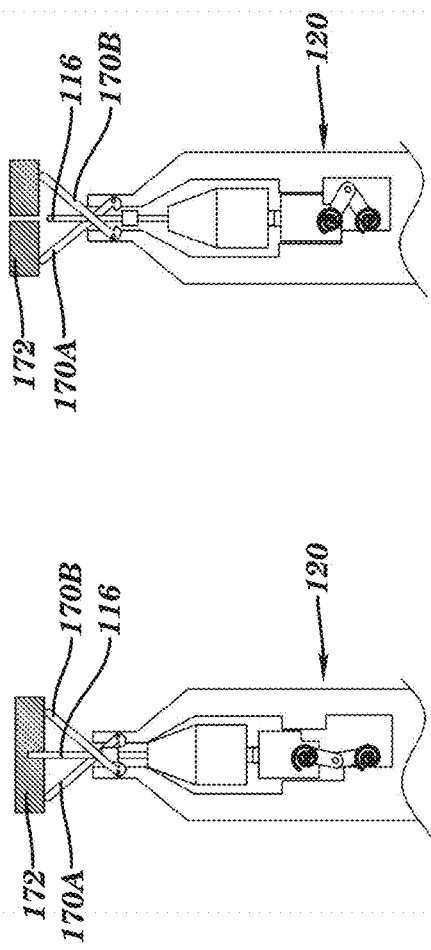

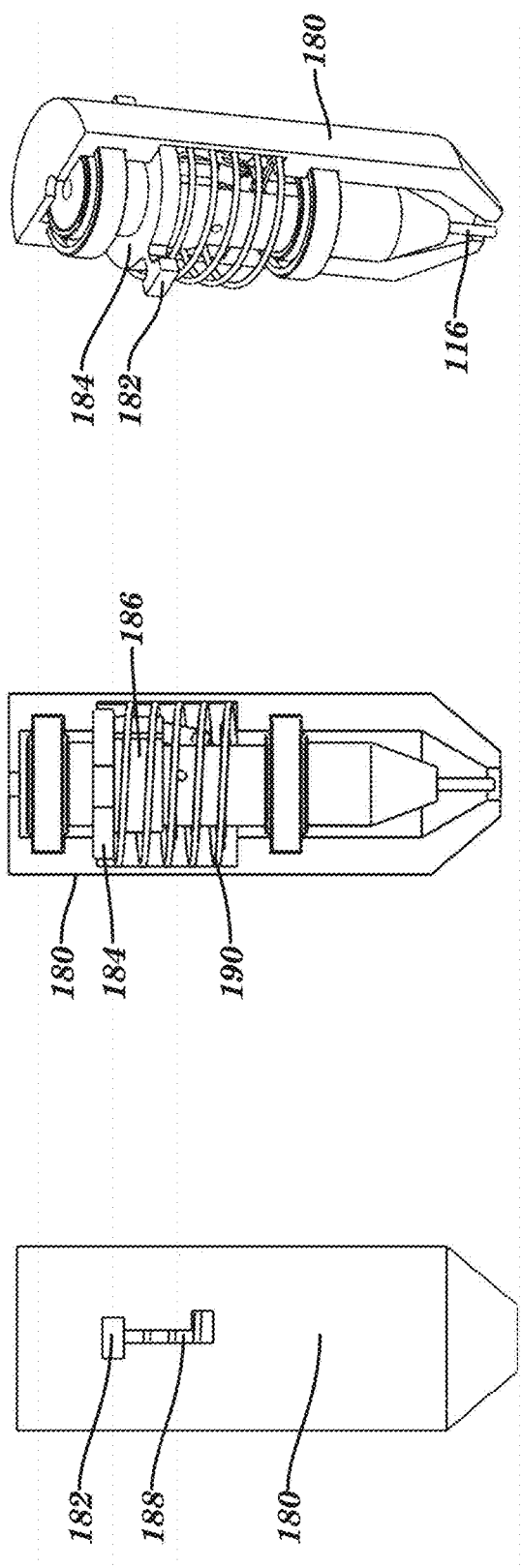

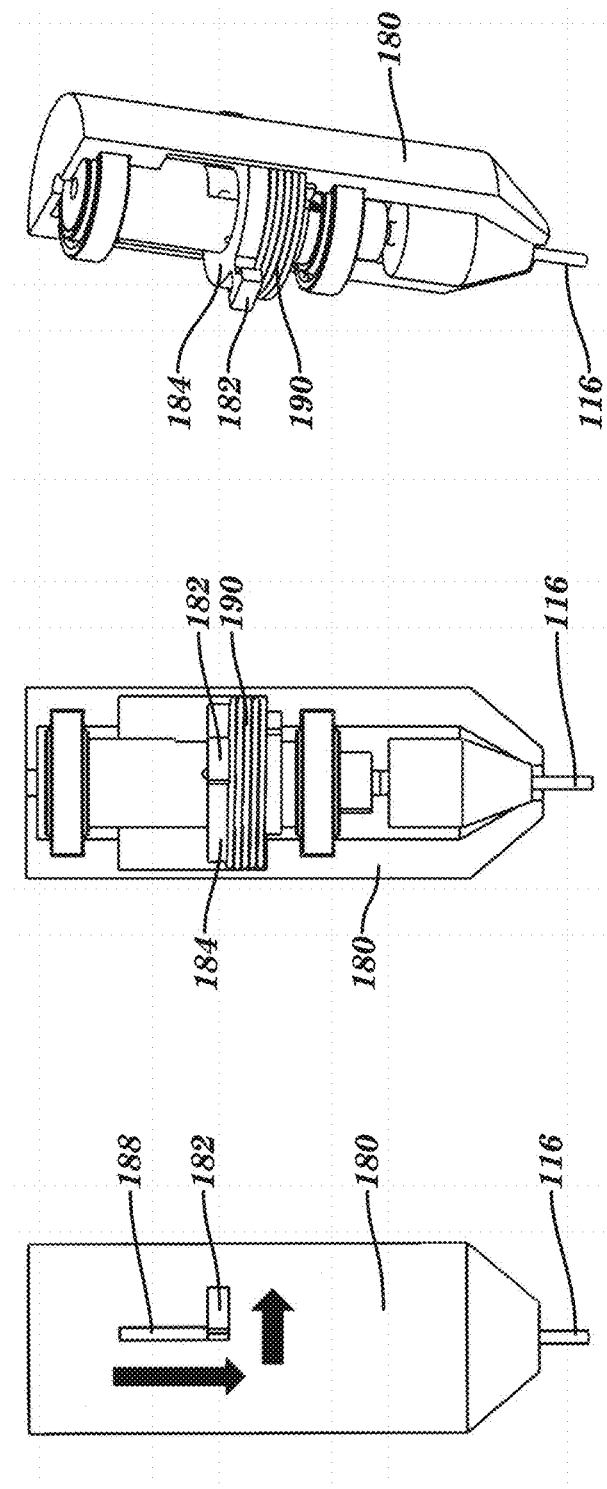

METHODS AND DEVICES FOR SAFELY PENETRATING MATERIALS

CROSS-REFERENCE TO RELATED APPLICATIONS

This Application is a 35 U.S.C. §371 National Phase Entry Application of International Application No. PCT/US2012/052470 filed Aug. 27, 2012, which designates the U.S., and claims the benefit of U.S. Provisional Application No. 61/527,585, filed Aug. 25, 2011, the contents of each of which are herein incorporated by reference in their entirety.

STATEMENT REGARDING FEDERALLY SPONSORED RESEARCH

This invention was made with government support under W81XWH-09-2-0001 awarded by U.S. Department of Defense. The government has certain rights in the invention.

REFERENCE TO MICROFICHE APPENDIX

Not Applicable

BACKGROUND

Technical Field of the Invention

The present invention is directed to controlling the penetration of instruments such as drills and needles being inserted into either hard or soft material. Specifically, the invention is directed to penetrating a material layer of unknown thickness without plunging into the adjacent material layer. In medical applications, the invention allows for drilling through bone without plunging into the adjacent soft tissue or for inserting a needle through one tissue layer (e.g. skin) without plunging into the adjacent softer tissue or body cavity.

Description of the Prior Art

In general, there are three forms of controllable drills found in the prior art: mechanical-control drills, electrical-control drills and ultrasonic drills. In medicine, cranial drills are used to drill through patients' skull to give direct access to the brain. Current cranial drills can be further divided into three categories: Mechanical-control drills (Drills without electronic control circuits; can be with or without auto-stop mechanism); Electrical-control drills (Drills that are automatically stopped with the use of sensors, presumably with control feedback); and Ultrasonic drills (Drills that vibrate a stationary or rotational cutting tool at a high frequency in the axial direction to chip away at hard surfaces, but have no effect on soft materials).

Mechanical Drills

Currently, physicians are using a variety of cranial drills in surgery. The drill can be manual or powered, with or without automatic stop. An experienced physician can, in general, safely use a drill without auto-stop mechanism, so normal drills are still popular in hospitals (although even the most experienced clinicians could make mistakes). Nevertheless, drills with safety mechanisms are necessary for areas without trained neurosurgeons to reduce the possibility of mistakes during operations. U.S. Pat. No. 2,842,131 appears to be the oldest patent about the automatic stop cranial drill, followed by U.S. Pat. Nos. 4,456,010, 4,699, 550, 4,803,982, 4,362,161, 4,600,006, and D596,743. Besides these, there are also other ways to make a drill safe: U.S. Pat. No. 5,382,250 uses an external stop to prevent drills from penetrating too far;

U.S. Pat. No. 2,842,131, entitled "Automatic Drill" describes a system of two concentric drill bores that have a clutch allowing them to spin in unison or not. The inside bore rotates and moves axially whereas the outer bore does not. This allows the inside bore to be compressed, engaging the rotational drive train, and the outer bore spins to create a shelf in the bone. When the inner bore breaks through the surface of the skull the clutch mechanism is released and both bores stop spinning. At this point, the outer bore rests on the shelf and the inner bore cannot proceed any farther. Products embodying this design are available from Acra-Cut. This product is used widely in operating room procedures where clinicians need access to the inside of the skull, but there are several limitations:

The size of the drill bits available by Acra-Cut are extremely limited. The outer bore cuts away extra bone unnecessarily. Further, the Acra-Cut tool must be powered by a pneumatic drill, which connects to an air hose and air compressor. Furthermore, if drilling with the Acra-Cut tool stops before penetration through the bone, then the rotation cannot recommence and thus a surgeon has to find an alternative means to finish penetrating the skull. These items are not easily made portable in emergency situations outside of the controlled operation room.

Additional patents using the same or similar concept of concentrically rotating drill bores that create a shelf for safety and contain a clutch mechanism include U.S. Pat. Nos. 4,362,161, 4,600,006, 4,803,982, 4,884,571, 5,135, 532.

U.S. Pat. No. 5,382,250, entitled Cranial Drill Stop, describes a hard stop that is set to the correct depth based on the thickness of the skull at the point of drilling. The interlocking spacers will make sure that only the proper length of drill bit is exposed. This could be a very effective safety method if the exact skull thickness is known at a certain anatomical location a priori. However skull thickness has been shown to vary widely across individual skulls and across race and gender. Thus if the stop is not adjusted correctly, it is not effective and potentially dangerous.

U.S. Pat. No. 6,716,215, entitled Cranial drill with sterile barrier, describes a sterile barrier system that can protect an MRI-compatible drill from coming in contact with patient fluids. The drill described in the patent is gas powered, much like the Acra-Cut, so that it cannot be used in emergency settings.

Currently there are no small caliber drills which have an automatic stop after penetrating bone. The only drill that stops automatically is the Acra-Cut, which cannot be used for small hole penetration. It is designed to create larger holes in the skull and there are many important procedures for which large holes are not necessary.

SUMMARY

The present invention is directed to a device for controlling the depth of a drilling operation and similar processes such as instrument insertion through layers of soft tissue. The invention includes a bi-stable coupling that can be used to allow a drill or other instrument to penetrate through a material layer of unknown thickness without plunging into the adjacent layer. In accordance with one embodiment of the invention, in a first state or position, force is applied to the bone by the drill bit to initiate cutting and a reactive force on the drill maintains the device in the first state and when drill bit penetrates the material, the reactive force is diminished enabling the device to transition to a second state or position in which the drill bit becomes retracted. In medical applications, the invention allows for drilling through bone of unknown thickness without plunging into the adjacent soft tissue.

In accordance with some embodiments of the invention, the invention includes a bi-stable coupling connected between the drive mechanism of a drilling device and the chuck that clamps on to the drill bit to transfer rotational force from the drive mechanism to the drill bit to rotate the drill bit about a longitudinal axis. The drive mechanism can include a hand crank for manual production of rotational force or a drive motor which use an energy source (e.g., electricity, pneumatic energy, hydraulic energy) to produce the rotational force that is applied to the drill bit. The bi-stable coupling can include at least two positions, a first position in which the coupling transfers a force along the longitudinal axis to the drill bit, urging the drill bit to penetrate the surface of some material and a second position in which the coupling retracts the drill bit, such as, inside a case away from the material.

In accordance with some embodiments of the invention, the bi-stable coupling can be embodied in a secondary drilling chuck that includes an input shaft adapted to be engaged by the chuck of a manual or motorized drill. The bi-stable coupling connects the input shaft to a second drill chuck that can clamp to a drill bit to transfer rotational force from the drill. This enables an existing drill to utilize the benefits of the present invention.

These and other capabilities of the invention, along with the invention itself, will be more fully understood after a review of the following figures, detailed description, and claims.

BRIEF DESCRIPTION OF THE FIGURES

FIGS. 6A and 6B are diagrammatic views of the linkage moving from the first position to the second position of a bi-stable coupling according to one embodiment of the invention.

FIGS. 12A and 12B show diagrammatic views of alternate embodiments of the invention employing magnets to provide a biasing force.

FIGS. 15A-C are diagrammatic views of the linkage moving from the first position to the second position of a bi-stable coupling according to one embodiment of the invention.

FIGS. 18A-E are partial diagrammatic views of a bi-stable coupling having a locking mechanism according to one embodiment of the invention.

FIG. 19A is a diagrammatic view of the initial configuration of a locking mechanism with the push ring in the second position according to one embodiment of the invention.

FIG. 19B is a cutaway view of FIG. 19A.

FIG. 19C is an isometric view of FIG. 19A.

FIG. 19D is a diagrammatic view of the motions needed to move the push ring into the first position such that the bi-stable coupling is locked into the first position.

FIG. 19E is a cutaway view of FIG. 19D.

FIG. 19F is an isometric view of FIG. 19D.

DETAILED DESCRIPTION OF PREFERRED EMBODIMENTS

The present invention is directed to a device for controlling the depth of a drilling operation and similar processes. The invention includes a bi-stable device that can be used to drill through a material layer of unknown thickness without plunging into the adjacent layer. In accordance with one embodiment of the invention, in a first state, force is applied to the drill bit to initiate cutting and a reactive force maintains the device in the first state and when drill bit penetrates the material, the reactive force is diminished enabling the device to transition to a second state in which the drill bit becomes retracted. In medical applications, the invention allows for drilling through bone of unknown thickness without plunging into the adjacent soft tissue.

Figure 1:
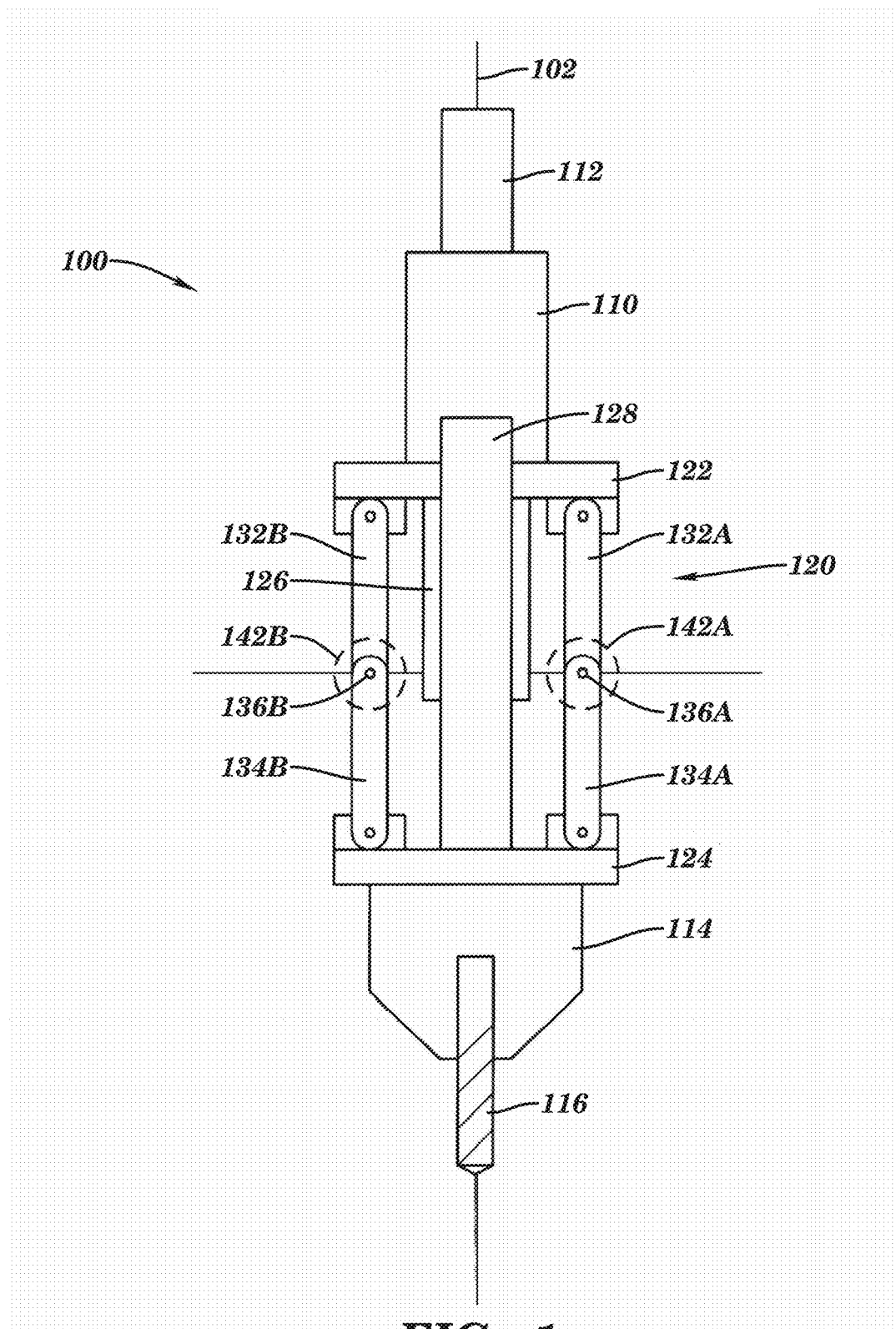
FIG. 1 is a diagrammatic view of a bi-stable coupling according to one embodiment of the invention.
Figure 2:
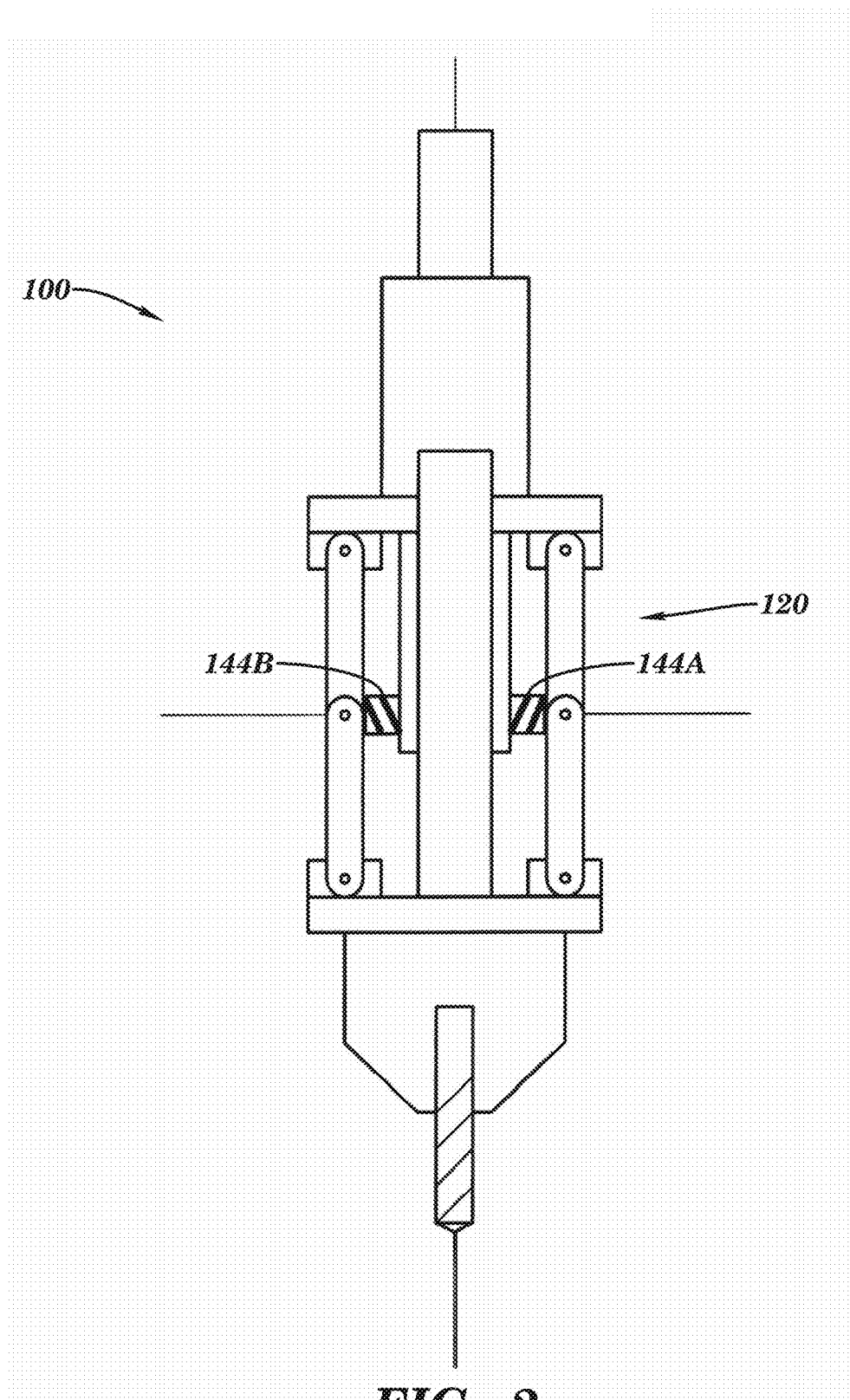
FIG. 2 is a diagrammatic view of a bi-stable coupling according to an alternate embodiment of the invention.
Figure 3:
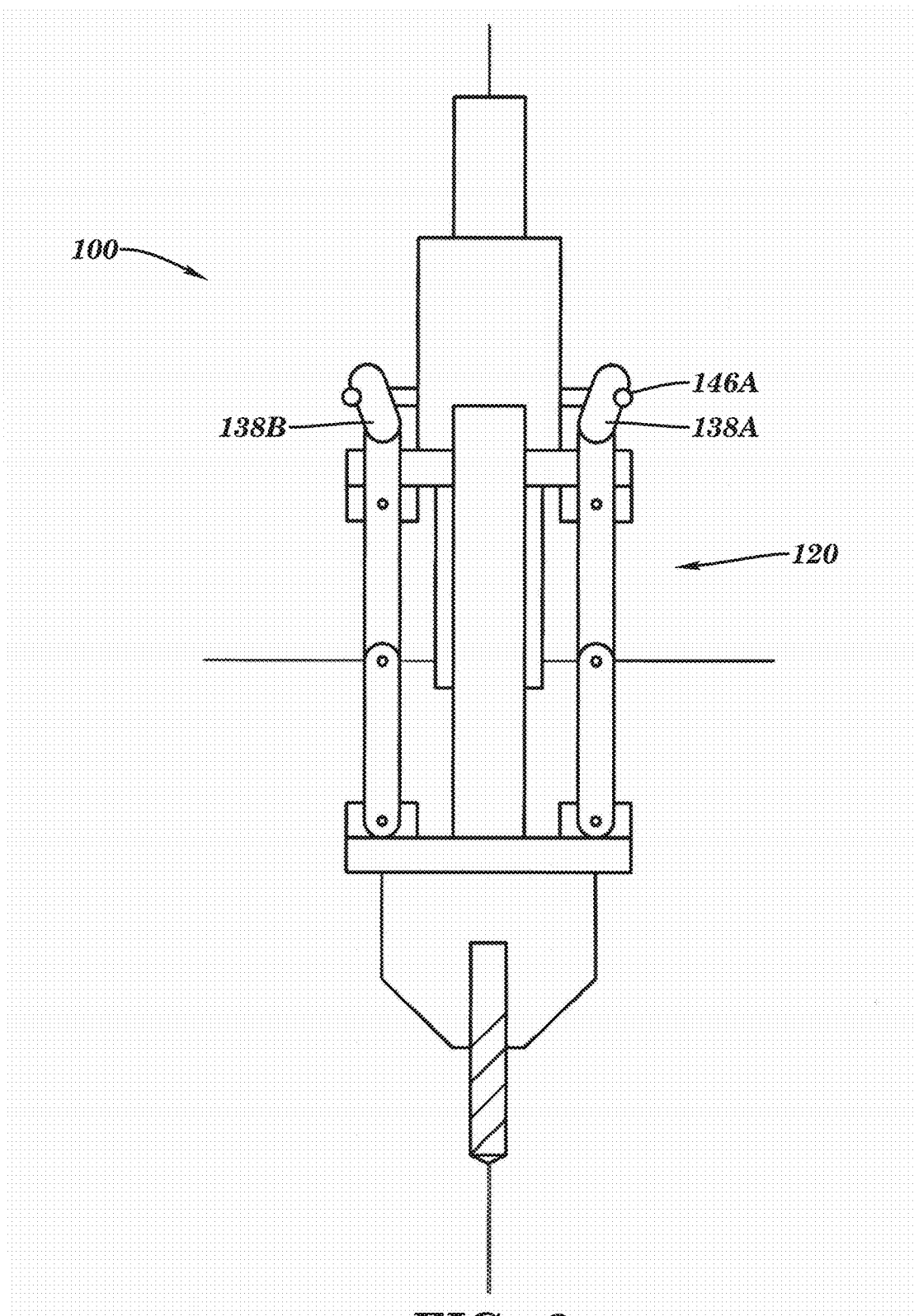
FIG. 3 is a diagrammatic view of a bi-stable coupling according to an alternate embodiment of the invention.

FIGS. 1, 2 and 3 show a diagram of a bi-stable device 100 according to various embodiments of the present invention. The device 100 extends along a longitudinal axis 102 and includes a leader 110 connected to a drill chuck 114 by a bi-stable coupling 120. The coupling 120 can include a first base member 122 coupled or fixed to the leader 110 and a second base member 124. The first base member 122 can include an opening 126 that receives a shaft member 128 of the second base member 124. The opening 126 and the shaft 128 serve to maintain the first base member 122 and the second base member 124 in alignment along the longitudinal axis 102. The opening 126 and the shaft 128 can be complimentary polygonal shaped, spline shaped or keyed such that they rotation force applied to the leader 110 drives the second base member 124, the drill chuck 114 and the drill bit 116 captured in the drill chuck 114. This configuration also allows the first base member 122 to move relative to the second base member 124 along the longitudinal axis 102.

The bi-stable coupling 120 further includes one or more linkages connecting the first base member 122 and the second base member 124. In accordance with one embodiment of the invention, two links can be used to connect the first and second base members 122 and 124. The linkage mechanism can include a first bar 132A pivotally connected at a first end to the first base member 122 and a second bar 134A pivotally connected at a first end to the second base member 124. The first bar 132A can also be pivotally connected at a second end to a second end of the second bar 134A by a central pivot joint. In this configuration, the central pivot joint can be moved radially with respect to the longitudinal axis 102 and enabling the second base member 124 to move relative to the first base member 122 along the longitudinal axis 102 and enabling the drill bit 116 to retract along the longitudinal axis.

In accordance with one embodiment of the present invention as shown in FIG. 1, the central pivot 136A can include a mass 142A that produces centrifugal force radially with respect to the longitudinal axis 102 on the central pivot 136A when the bi-stable coupling 120 is rotated. The centrifugal force causes the central pivot 136A to move radially outward from the longitudinal axis 102 causing the drill bit to be retracted. In operation, the central pivot 136A is oriented inward, closer to the longitudinal axis 102 than the other pivot points, the drill bit is placed in contact with the surface to be drilled and the force applied from the drill to the drill bit holds the linkage in place in the first position until the drill bit penetrates the material and the reaction force is removed. When the reaction force is removed, the centrifugal force of the mass 142A is able to drive the central pivot 136A radially outward to the second position causing the drill bit to retract.

In accordance with an alternate embodiment of the present invention as shown in FIG. 2, instead of providing a mass 142A, the bi-stable coupling 120 can include one or more springs 144A that are positioned apply a force radially outward to drive the linkage outward, and cause the central pivot 136A to move radially outward from the longitudinal axis 102 beyond the other pivot points causing the drill bit to be retracted. In operation, the central pivot 136A is oriented inward, closer to the longitudinal axis 102 than the other pivot points, the drill bit is placed in contact with the surface to be drilled and the force applied from the drill to the drill bit holds the linkage in place in the first position until the drill bit penetrates the material and the reaction force is removed. When the reaction force removed, the force of the spring 144A is able to drive the central pivot 136A radially outward to the second position causing the drill bit to retract. While FIG. 2 shows that the springs as coiled compression springs, other types and forms of springs can be used.

Figure 13:
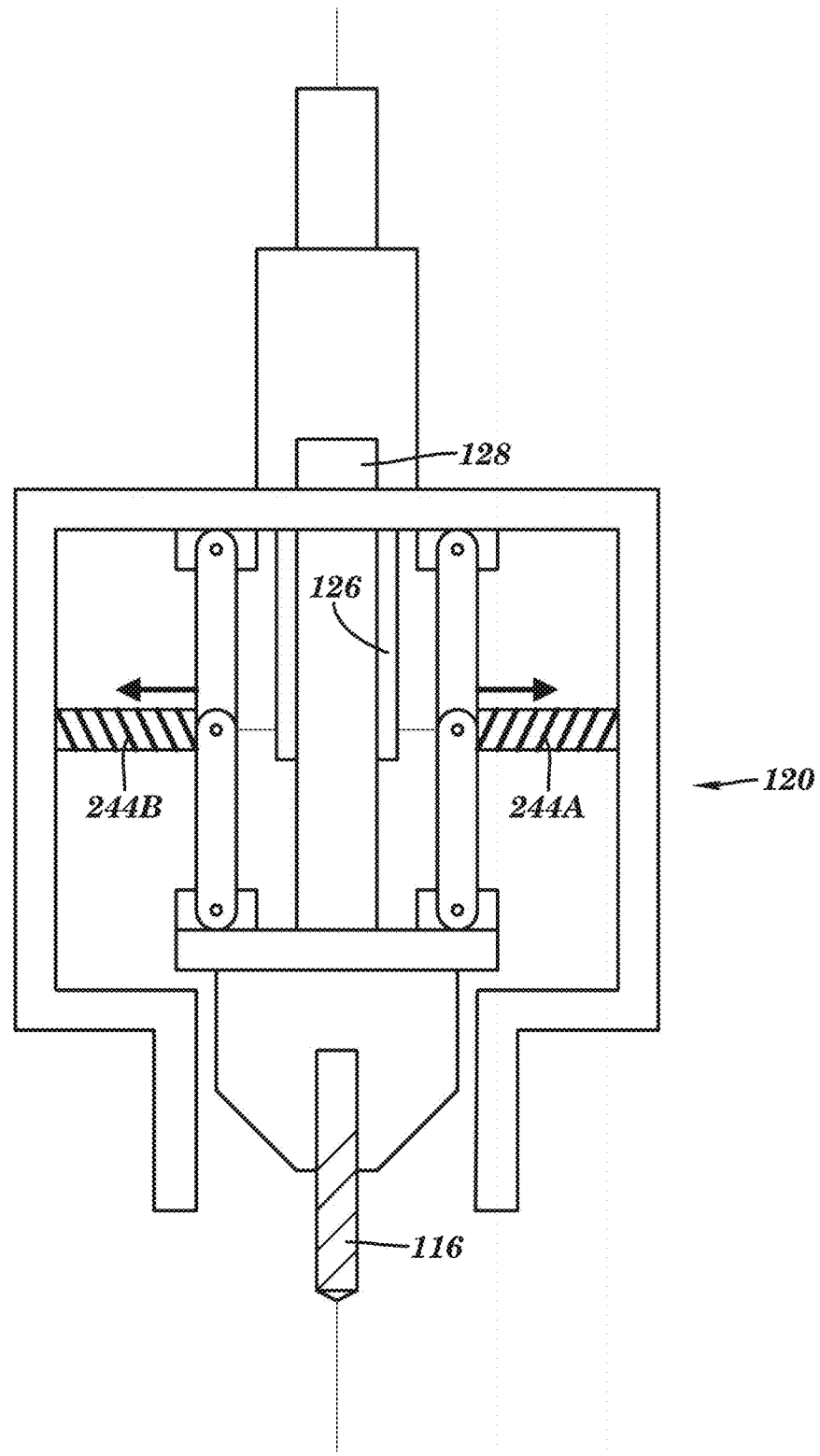
FIG. 13 shows an alternative embodiment of the present invention.

For example, in FIG. 13, linear springs 244A, 244B extend perpendicularly from the shaft 128 or sleeve 126. This arrangement can be used to bias the linkage radially outward from the longitudinal axis. Therefore, in the first position, linear springs 244A, 244B have stored energy in either compression or extension depending on whether the spring is anchored to the sleeve 126 or the shaft 128. In the absence of a normal force at the drill bit 116, the stored spring energy drives the mechanism to the second position. Alternatively, a torsional spring at the central pivot 136A can also be used to bias the linkage radially outward from the longitudinal axis, as shown and described below with respect to FIGS. 15A-C.

In accordance with another embodiment of the present invention as shown in FIGS. 15A-C, the bi-stable coupling 120 can include one or more torsional springs 154A, 154B that are positioned at the link joints to create resistive forces. When the bi-stable coupling 120 is in the first position as shown in FIG. 15A, the torsional springs 154A, 154B are applying a restoring force to return the mechanism to the second position, as shown in FIG. 15C. FIG. 15B illustrates the transition of the bi-stable coupling 120 between the first position and the second position. This embodiment, therefore, does not rely on the rotation speed of the tool to generate centrifugal forces large enough to cause retraction when the force is removed from the tool tip. Further, the embodiments shown in FIGS. 15A and 15C allow the position of the base to be adjusted. In the case of FIG. 15A, movement of the base changes the angle, Θ, between the first bar 132A and the second bar 134A of the linkage mechanism in the first position, which can be used to increase or decrease the sensitivity of the device to changes in applied normal force at the tool tip. In the case of FIG. 15C, movement of the base can be used to increase or decrease the amount of retraction.

Figure 16:
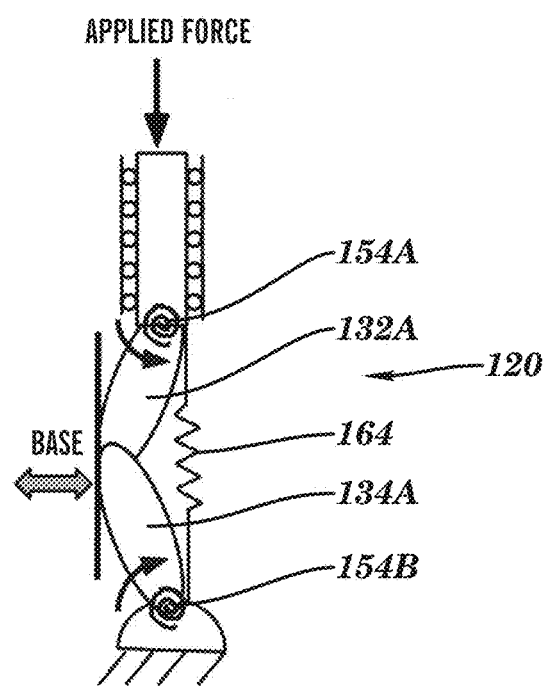
FIG. 16 is a diagrammatic view of the linkage in the first position of a bi-stable coupling according to an alternate embodiment of the invention.

In still another embodiment of the present invention as shown in FIG. 16, the bi-stable coupling 120 of FIGS. 15A-C can further include a linear spring 164 between the torsional springs 154A, 154B. In this embodiment, the retraction force of the bi-stable coupling 120 is increased.

In other embodiments, other mechanisms for applying forces can be used. For example as shown in FIGS. 12A and 12B, a pair of magnets can be used to bias the linkage radially outward from the longitudinal axis, either using opposite poles to attract and drive the central pivot 136A radially outward or using the same poles to repel and drive the central pivot 136A radially outward.

In accordance with an alternate embodiment of the present invention as shown in FIG. 3, the first bar 132A includes an extension 138A and the bi-stable coupling 120 can include one or more elastic bands or springs 146A that are positioned apply a force radially inward to drive the extension 138A inward, and cause the central pivot 136A to move radially outward from the longitudinal axis 102 beyond the other pivot points causing the drill bit to be retracted. In operation, the central pivot 136A is oriented inward, closer to the longitudinal axis 102 than the other pivot points, the drill bit is placed in contact with the surface to be drilled and the force applied from the drill to the drill bit holds the linkage in place in the first position until the drill bit penetrates the material and the reaction force is removed. When the reaction force removed, the force of the elastic bands or springs 146A is able to drive the central pivot 136A radially outward to the second position causing the drill bit to retract.

In accordance with other embodiments of the invention, the bi-stable coupling can use a combination of masses (142A), spring (144A) and/or elastic bands (146A) together to bias the linkage mechanism into the appropriate position at the appropriate time.

In accordance with some embodiments of the invention as shown in FIG. 13, the bi-stable coupling can include a housing that enables the cutting or penetrating tool to retract into the housing away from the surface or material to be penetrated after the tool penetrates the intended layer. The housing can include an element that contacts the surface to enable the tool to be retracted.

As will be explained in more detail, the dimensions of the components and the forces of the springs will vary greatly depending on the application and use of the invention. Factors, such as the hardness or softness of the material to be drilled, and the size and depth of the hole can influence the design preferences for the coupling.

In accordance with one embodiment, the invention can be used to drill a hole in the skull without plunging the drill bit into brain tissue. The following description provides a more detailed description for selecting the design parameters for the coupling for this exemplary application of the invention.

Figure 4:
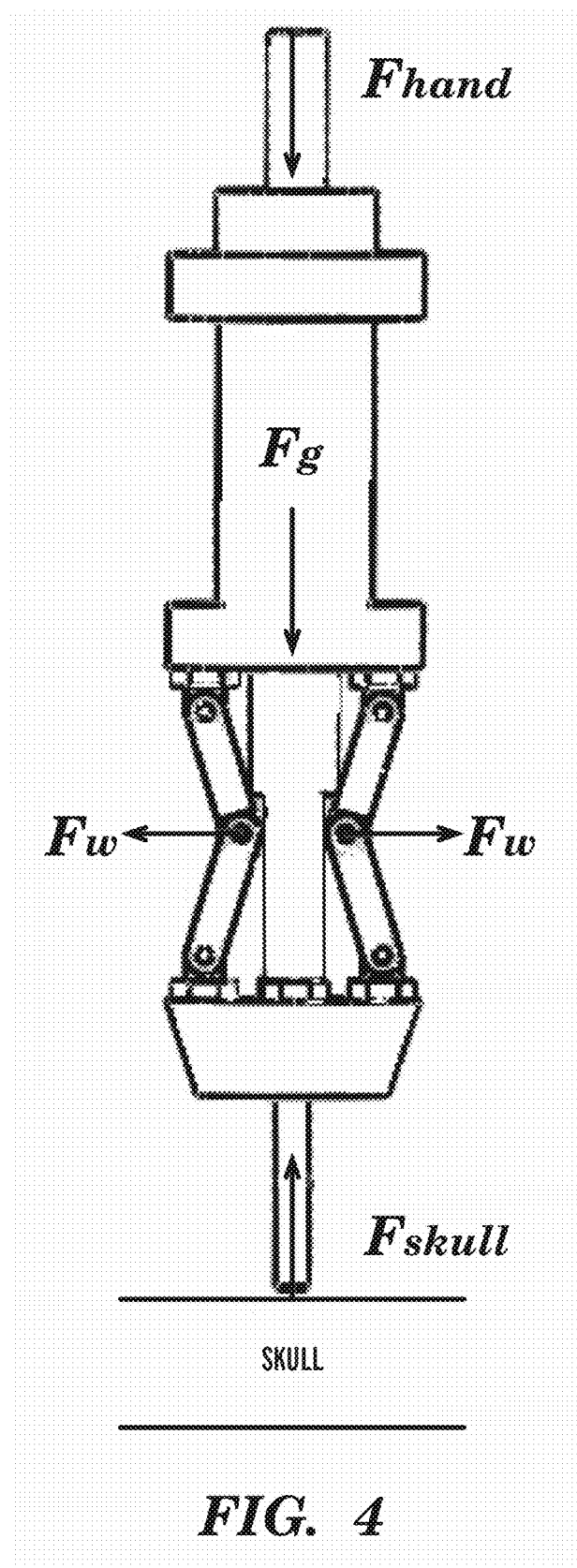
FIG. 4 is a diagrammatic view of forces acting on a bi-stable coupling according to one embodiment of the invention.

As shown in FIG. 4, the forces acting on the system consist of several components when the drill is vertically oriented and directed downward towards the skull. $F_{hand}$ is the force applied by the clinician's hand, $F_g$ is the gravitational force of the drill, $F_\omega$ is the centrifugal force due to the spinning masses, and $F_{skull}$ is the reaction force from the skull being drilled. The force balance equation in the vertical direction is given by Equation 1. Equation 2 calculates the centrifugal force based on $m_0$, the mass of the weights, $\omega$, the spinning speed of the drill, and r, the distance from the mass to the rotational axis of the drill.

$$F_{hand} + F_g = F_{skull} \qquad (1)$$

$$F_\omega = m_0 \omega^2 r \qquad (2)$$

Figure 5:
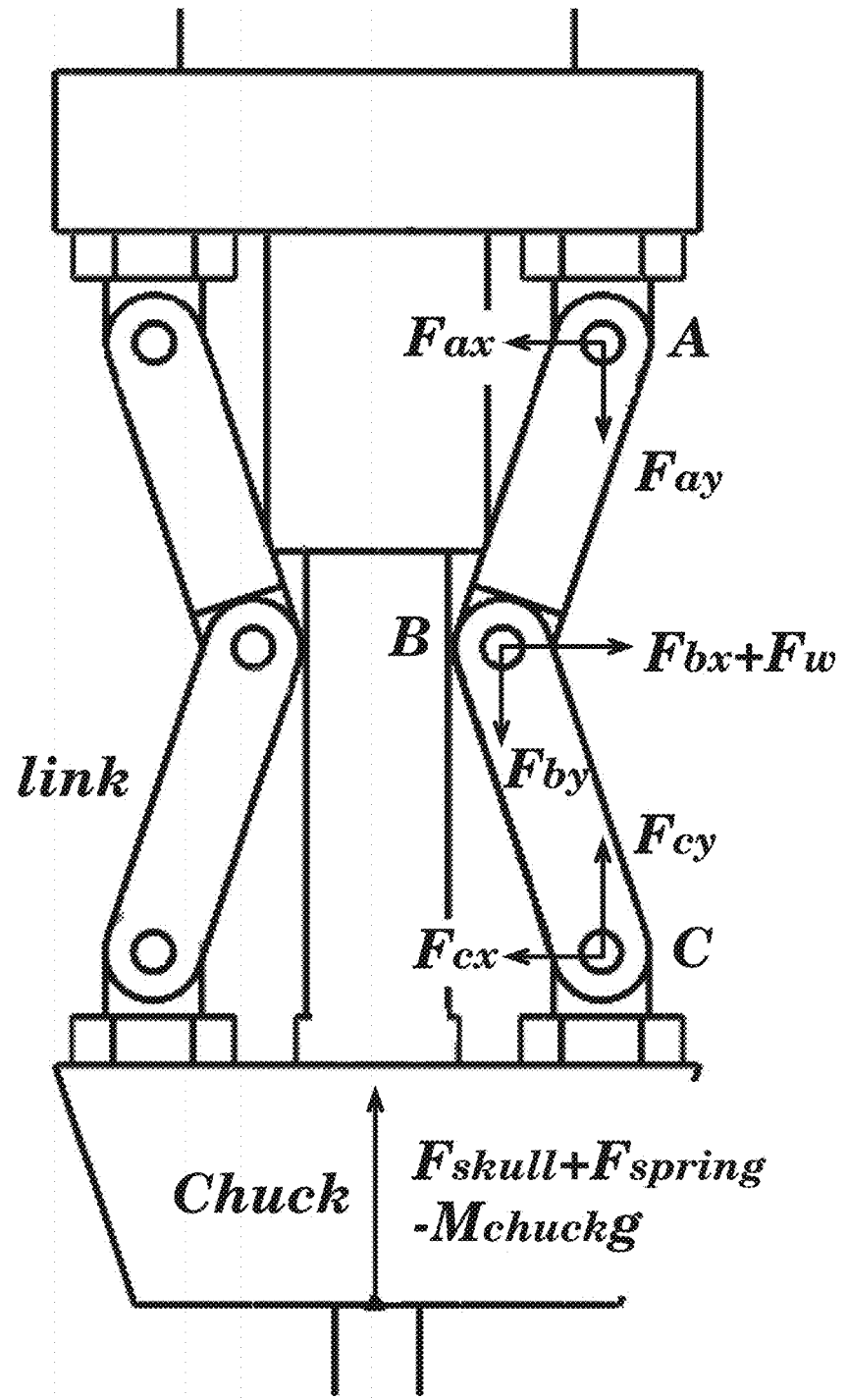
FIG. 5 is a diagrammatic view of the structure of the linkage and forces being applied to a bi-stable coupling according to one embodiment of the invention.

FIG. 5 shows the structure of one linkage of the device (Points A-B-C) and the forces being applied to it. Due to symmetry, only one pair of links needs to be analyzed. All forces acting on the links are noted by labeled arrows. The vertical force being applied to point C ($F_{cy}$) is given by Equation 3, which is half of the summation of the reaction force from the skull, $F_{skull}$, the compressive force of the spring, $F_{spring}$, and the gravitational force of the chuck, $M_{chuck}g$. The vertical force balance for the linkage is then given by Equation 4. The horizontal force balance for the linkage is given by Equation 5.

$$F_{cy} = \frac{F_{skull} + F_{spring} - M_{chuck}g}{2} \qquad (3)$$

$$F_{ay} = F_{cy} - m_0 g \qquad (4)$$

$$F_{cx} + F_{ax} = F_\omega + F_{bx} \qquad (5)$$

Next, the moment balance for link A-B is calculated. The torque caused by $F_{ax}$ and $F_{ay}$ with respect to point B should balance each other, resulting in Equation 6, where $\theta$ is the angle between one link and the shaft (see FIG. 9). Similarly, the moment balance for link B-C with respect to point B is given by Equation 7.

$$F_{ax} l \cos\theta = F_{ay} l \sin\theta \qquad (6)$$

$$F_{cx} l \cos\theta = F_{cy} l \sin\theta \qquad (7)$$

Equations 1-7 can be combined and arranged to solve for $F_{bx}$ as in Equation 8.

$$f_{bx} = (F_{skull} + F_{spring} - (M_{chuck} + m_0)g)\tan\theta - m_0 \omega^2 r \qquad (8)$$

The physical meaning of the reaction force $F_{bx}$ is quite important. If $F_{bx}$ is positive the linkage is forced inward and point B is being supported by the shaft. As shown in FIGS. 4 and 5, the device is in the drilling "closed" or first position. However, if $F_{bx}$ becomes negative, the shaft is no longer supporting point B. Rather than remaining in contact with the shaft, point B will begin to move outwards and the links will pop-out to the collapsed "open" or second position. The next step is to determine the relationship between $F_{skull}$ and the configuration of the linkage by inserting positive $F_{bx}$ in to Equation 8 and solving for $F_{skull}$, where $F_{cr}$ is the critical force defined by Equation 9.

$$F_{skull} > m_0 \omega^2 r \frac{1}{\tan\theta} + (M_{chuck} + m_0)g - F_{spring} \triangleq F_{cr} \qquad (9)$$

If Equation 9 is true and $F_{skull}$ exceeds $F_{cr}$ the links will be kept in the drilling or first position. If Equation 9 is not satisfied (if $F_{skull} < F_{cr}$) then the links will collapse into the open or second position. Equation 9 requires pushing force to be maintained by the clinician during the drilling process to ensure that the links do not open before drilling is finished. Upon skull penetration the reaction force of the skull will reduce significantly [13], such that $F_{skull} < F_{cr}$. This change in the reaction force will cause the linkage to collapse, therefore retracting the drill bit the proper distance. Dynamics of Bi-stable Mechanism The maximum penetration distance, $L_{push}$, is the total distance traversed by the drill bit towards brain tissue after penetrating the skull. FIGS. 6A and 6B show diagrams of the linkage just before and upon penetration. Since $F_{skull}$ becomes zero at this point, the linkage is no longer in equilibrium state, and a net horizontal force, $F_{out}$, is applied to the mass attached to point B. Equations 9 and 10 calculate the net force and acceleration of point B.

$$F_{out} = m_0 \omega^2 r + [(M_{chuck} + m_0)g - F_{spring}]\tan\theta \qquad (10)$$

$$a_{out} = \frac{F_{out}}{m_0} \qquad (11)$$

While point B moves to the right and the linkage approaches the parallel position in FIG. 6B, the distance that point B travels, $l_{pop}$, is calculated by Equation 12. The time needed to travel this distance is calculated in Equation 13.

$$l_{pop} = l\sin\theta \qquad (12)$$

$$\Delta t = \sqrt{\frac{2 l_{pop}}{a_{out}}} \qquad (13)$$

During time $\Delta t$, the whole drill vertically accelerates forward due to the continued pushing force by the doctor. This vertical acceleration is calculated by Equation 14 where $M_{total}$ is the mass of the whole assembly.

$$a_{push} = \frac{F_{skull}}{M_{total}} \qquad (14)$$

From Equations 11-14, the downward distance traversed by the whole drill before linkage collapse can be calculated by solving $L_1$ in Equation 15. Meanwhile, as the linkage moves from closed position to parallel position, point C will move forward relative to point A by distance $L_2$ calculated in Equation 16. Together, the maximum penetration distance is the sum of these two distances calculated in Equation 17.

$$L_1 = \frac{1}{2} a_{push} \Delta t^2 \qquad (15)$$

$$= \frac{F_{skull}}{F_{out}} \frac{m_0}{M_{total}} l\sin\theta$$

$$L_2 = 2l(1 - \cos\theta) \qquad (16)$$

$$L_{push} = L_1 + L_2 \qquad (17)$$

$$= \left[\frac{F_{react} - F_{remain}}{F_{out}} \frac{m_0}{M_{total}} \sin\theta + 2(1 - \cos\theta)\right]l$$

Selecting Design Parameters

To design a drill that can work safely and comfortably, the following factors need to be considered:

Retraction Distance

The retraction distance, $L_{back}$, is the distance that the drill bit retracts. As the linkages collapse and changes from closed to open position, the retraction distance, $L_{back}$, of the drill bit can be calculated by Equation 18 where α is the angle between the link and the shaft in the fully open position. After penetration the whole drill bit should be able to fully retract from the skull, so $L_{back}$ should be larger than a typical large skull thickness.

$$L_{back} = 2l(\cos\theta - \cos\alpha) \quad (18)$$

$$L_{back} > 10 \text{ mm} \quad (19)$$

Penetration Distance

To ensure that the drill bit does not damage brain tissue after penetrating the skull, the maximum penetration distance $L_{push}$ should be less than 2 mm.

$$L_{push} < 2 \text{ mm} \quad (20)$$

Critical Force

The critical force, $F_{cr}$, was calculated in Equation 9 as the lower limit of $F_{skull}$ in the drilling position. Below $F_{cr}$ the linkage will collapse to open position. Therefore $F_{cr}$ must be designed as the lower limit of clinicians' typical drilling forces so that the device continues drilling within the comfortable range for doctors to operate. Depending on the size of the drill bit, the feed rate, and the application, typical pushing force can range from 10 N to 40 N. The system can be designed to function correctly within this broad approximate range of pushing forces.

$$F_{cr} \leq 10\text{N} \quad (21)$$

Table II contains the optimal set of design parameters that can satisfy Equations 19-21. These parameters were used in the final prototype, which will be discussed in the next section.

TABLE II

Design Parameters

| $M_{total}$ | 2.5 kg | $L_{back}$ | 11.6 mm |
|---|---|---|---|
| $M_{chuck}$ | 60 g | $L_{push}$ | 0.64 mm |
| $m_0$ | 10 g | $F_{cr}$ | 10.2N |
| θ | 10° | $F_{skull}$ | 50N |
| α | 60° | $F_{spring}$ | 10N |
| r | 16 mm | w | 1400 rpm |
| l | 12 mm | | |

Sensitivity Analysis

The value $L_{push}$ is a useful variable in the analysis and for calculating the sensitivity of the mechanism. Table III was determined by changing each of the parameters listed by ±1% and calculating the resulting change in $L_{push}$. An increase in θ, l, $F_{spring}$, or a decrease in r, w, $m_0$ will all lead to a larger $L_{push}$. It is evident from the table that $L_{push}$ is most sensitive to θ and w. Therefore, the part dimension that determines θ must be especially accurate to ensure that the experimentally determined $L_{push}$ does not exceed the calculated value. The drill used to spin the device should have rotational speed minimum 1400 rpm to ensure a smaller and safer $L_{push}$.

TABLE III

Sensitivity Analysis
Error of $L_{push}$ due to ±1% change

| θ | ±1.97% | r | ∓0.86% |
|---|---|---|---|
| w | ∓1.72% | $F_{spring}$ | ±0.44% |
| l | ±1.01% | $m_0$ | ∓0.4% |

EXAMPLES

Based on the above analysis, an embodiment of the bi-stable mechanism according to the invention was created. A number of different mechanical designs can be developed and then the component layout and robust connections among different parts, such as masses, links, chuck and leader, can be optimized in order to make the drill more compact and easier to manufacture and assemble.

Figure 7:
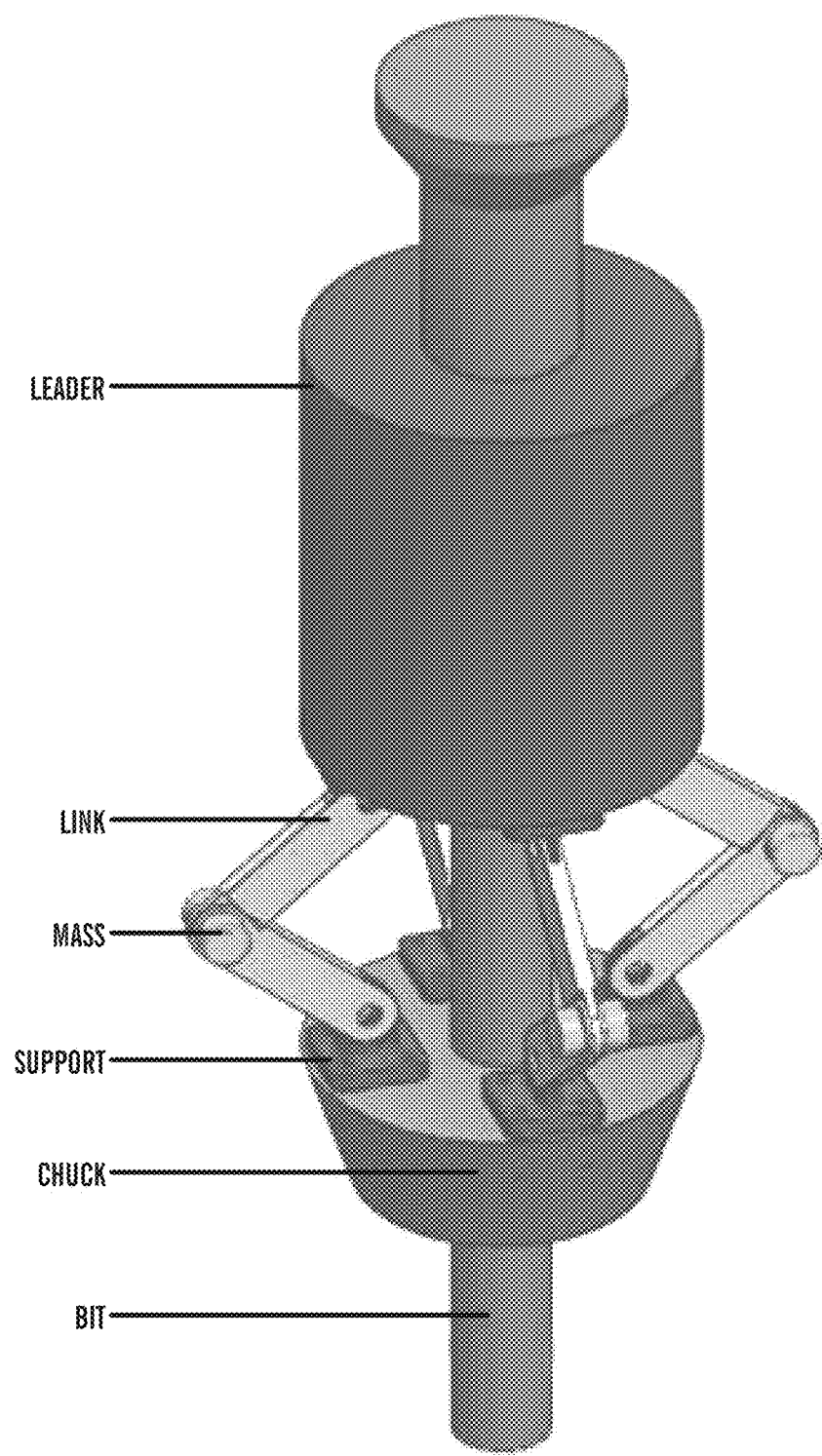
FIG. 7 is a diagrammatic view of a bi-stable coupling according to an alternate embodiment of the invention.
Figure 8:
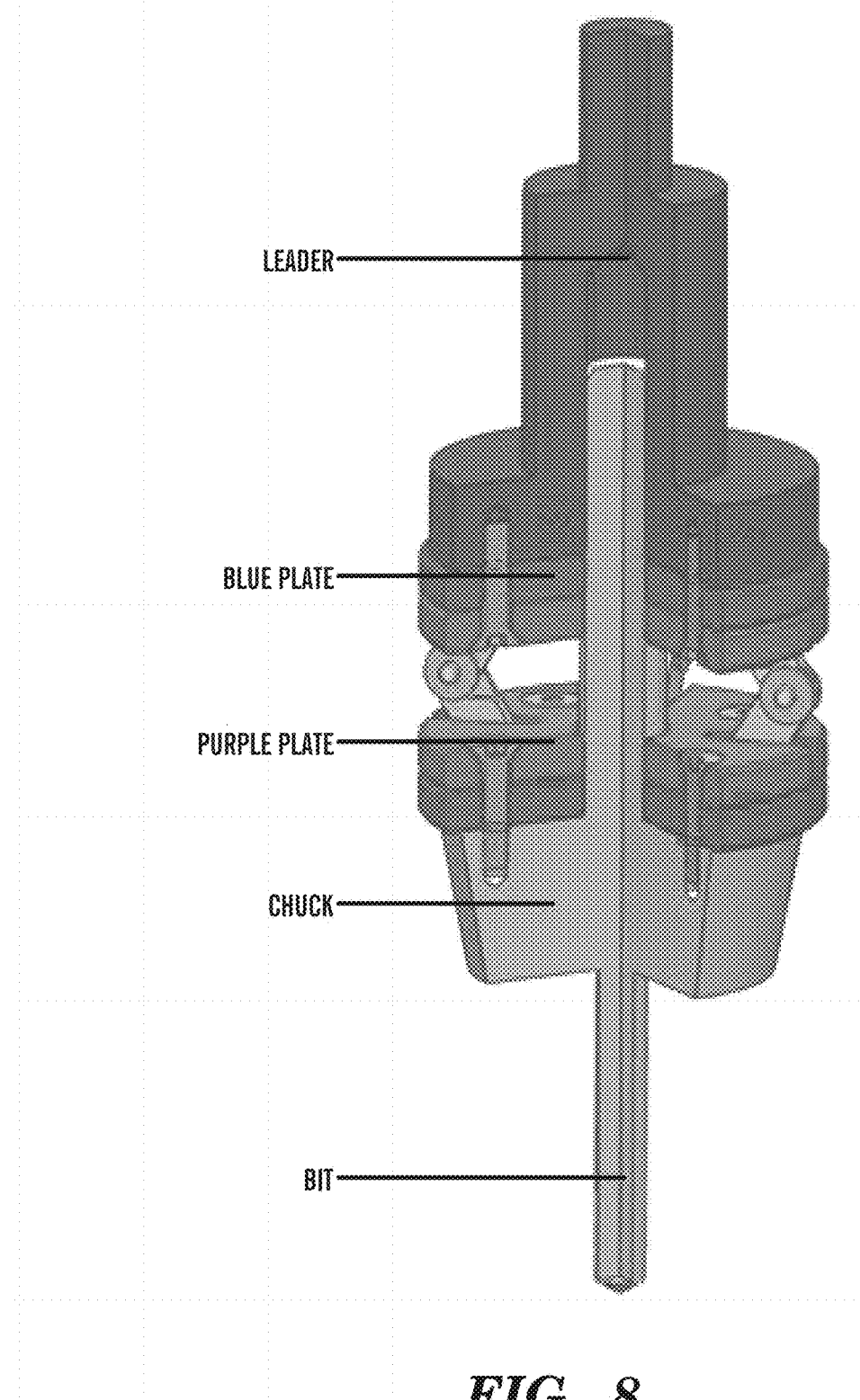
FIG. 8 is a diagrammatic view of a bi-stable coupling according to an alternate embodiment of the invention.

Many parts of the device can be resized to make the device as compact as possible without sacrificing material strength. The total number of parts can be minimized to reduce manufacturing costs. In accordance with one embodiment, the links were sized to retract the drill bit by 11 mm. In one embodiment, the links were inserted into grooves containing steel shafts (pivot pins) for link rotation. A cylinder concentric to the shaft was added to ensure that the desired angle between the links and the shaft is accurate and precise. Various embodiments of bi-stable coupling according to the invention are shown in FIG. 7, FIG. 8, FIG. 9, and the final prototype FIG. 10.

In accordance with the invention, the bi-stable coupling can be adapted to connect directly to the drive shaft of a drill, for example by providing an internal or external thread on the leader 110 to enable it to be mounted on the drive shaft of a motor and thus having one device all packaged together. Alternatively, the leader 100 can include an extension shaft 112 that can be inserted into the chuck of a drill. In this embodiment, the device according to the invention includes a second chuck for retaining the drill bit.

Figure 9:
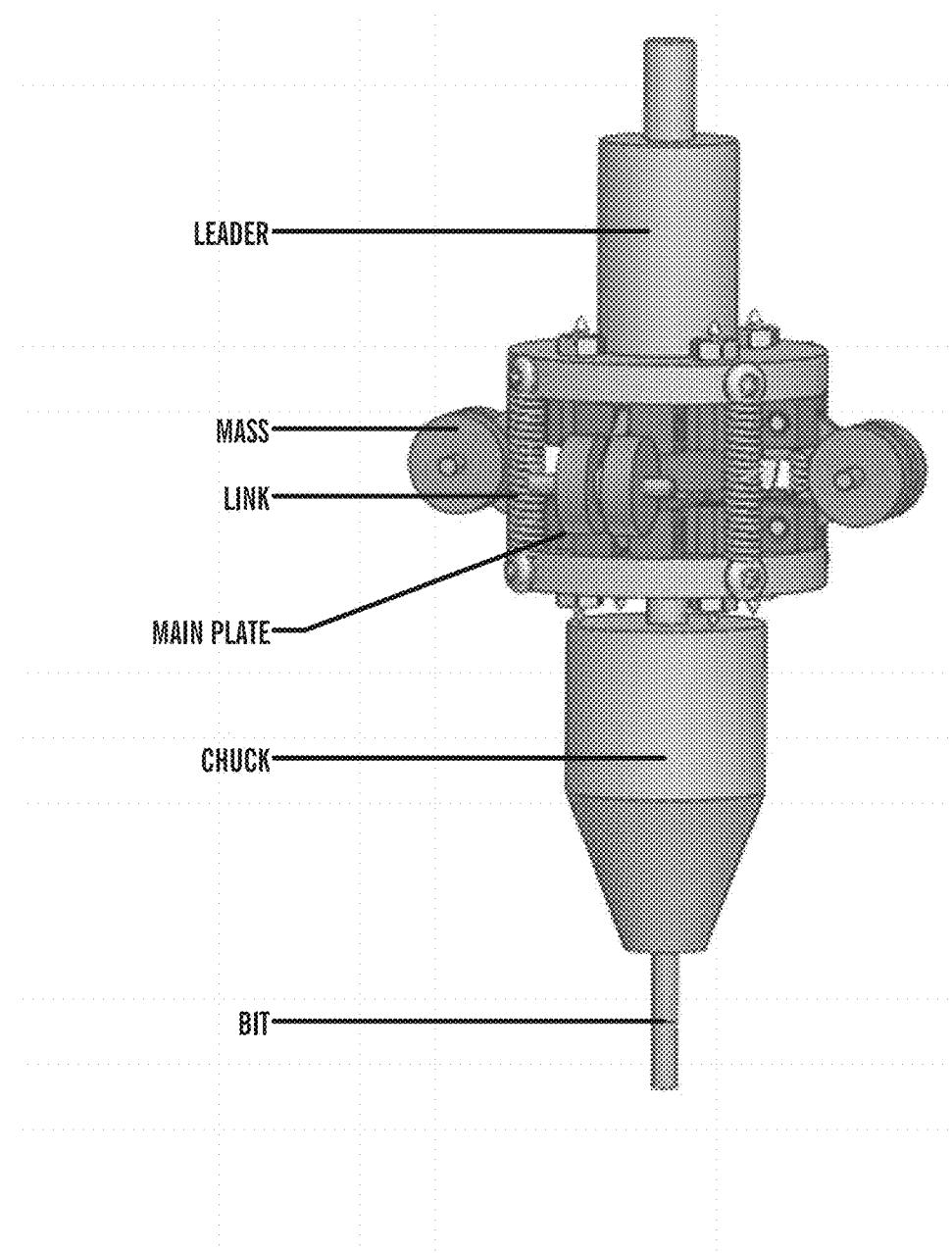
FIG. 9 is a diagrammatic view of a bi-stable coupling according to an alternate embodiment of the invention.
Figure 10A:
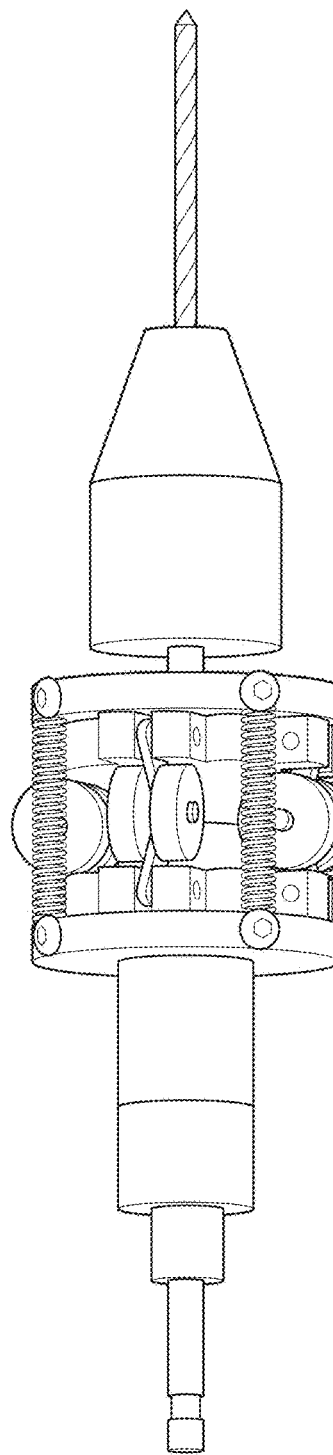
FIGS. 10A and 10B are diagrammatic views of a bi-stable coupling according to an alternate embodiment of the invention
Figure 10B:
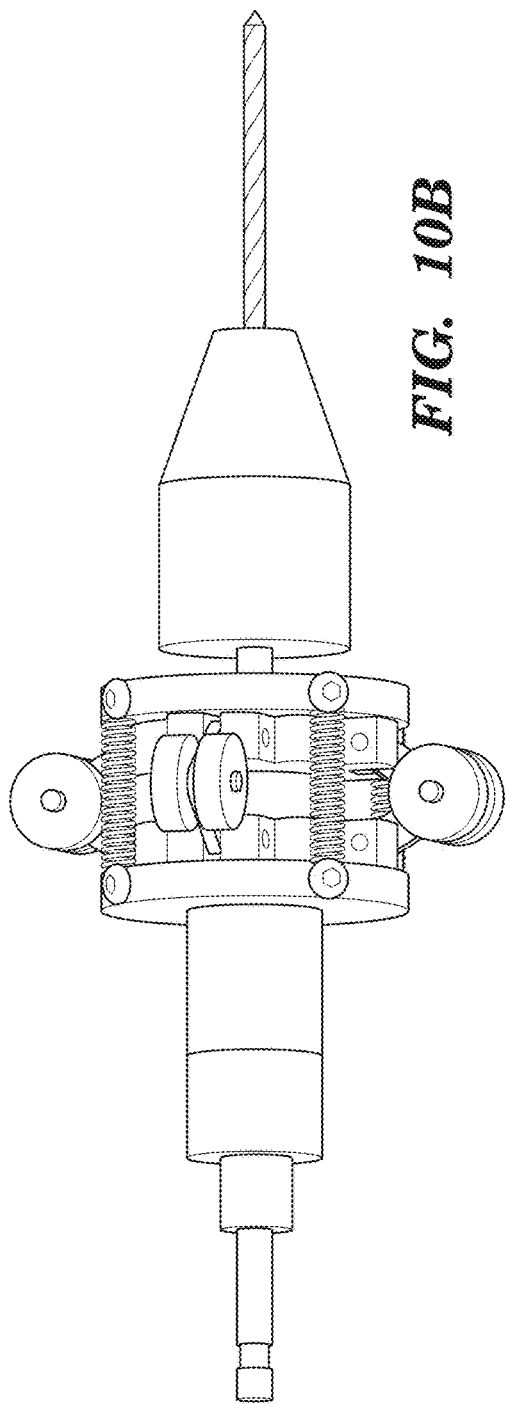

FIGS. 9 and 10 show alternative embodiments of the present invention that include one or more springs connecting the first base member with the second base member and serves to bias the bi-stable coupling into the open or second position. In this embodiment, the spring(s) also serves to hold the bi-stable coupling in the closed or first position after the first base member and the second base member are separated and the central pivot of each link is moved into the closed or second position. In operation, the masses are selected, such that at the intended rotational speed, the centrifugal force is sufficient to overcome bias of the spring to stay in the closed or first position when there is no reaction force from drilling into a material.

Figures 14A, 14B, 14C:
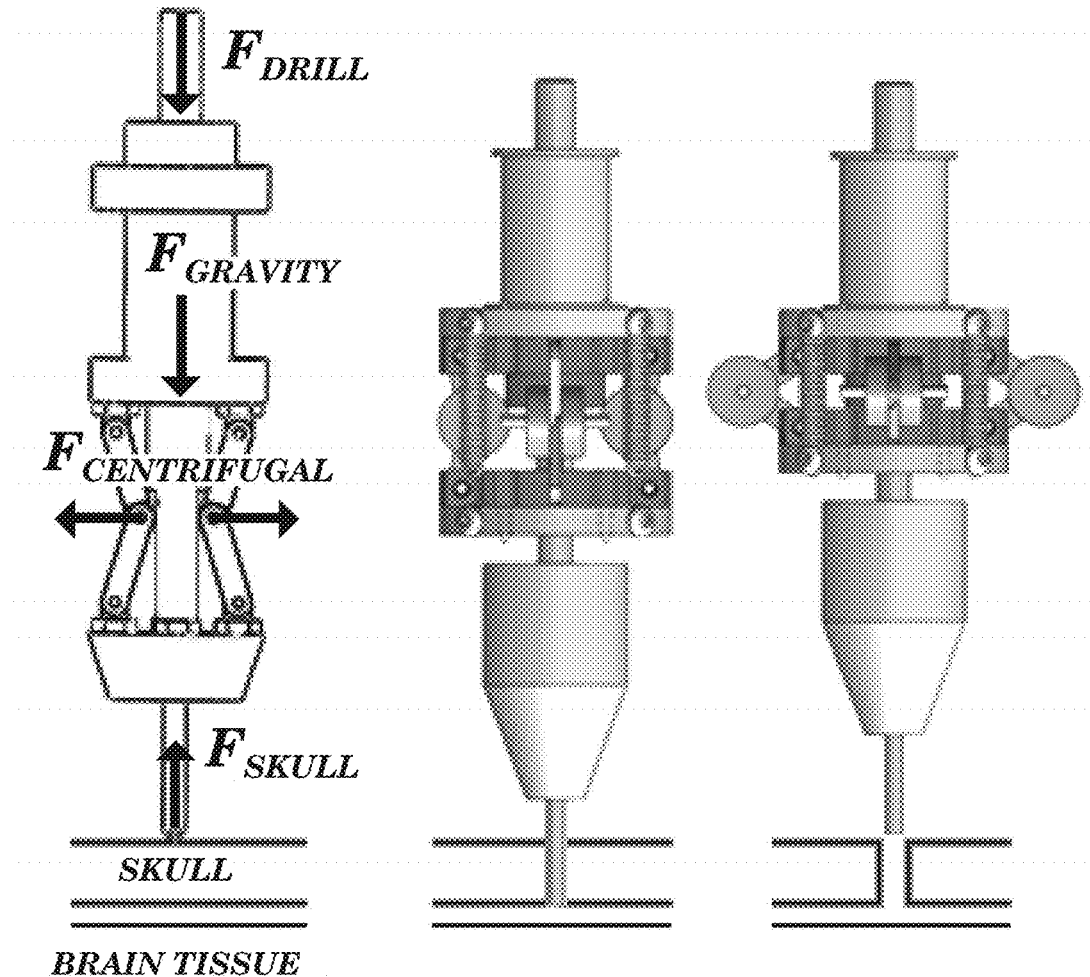
FIG. 14 shows a diagram of an application of an embodiment of the invention.

The various embodiments of present invention can utilize a dynamic bi-stable mechanism that supports drilling when force is being applied to the drill (see FIG. 14b, the "drilling" position) but retracts inside a protective sheath (not shown) when the force is reduced by penetrating the skull (FIG. 14c, "collapsed" position). The bi-stable mechanism is activated by centrifugal forces (due to drill rotation) in FIG. 14a that cause the linkages to change from drilling position to collapsed position at the moment of skull penetration. Initial testing on ex-vivo animal structures has verified that the retraction mechanism successfully removes the drill bit before damaging soft tissue beneath the skull.

Figure 17A:
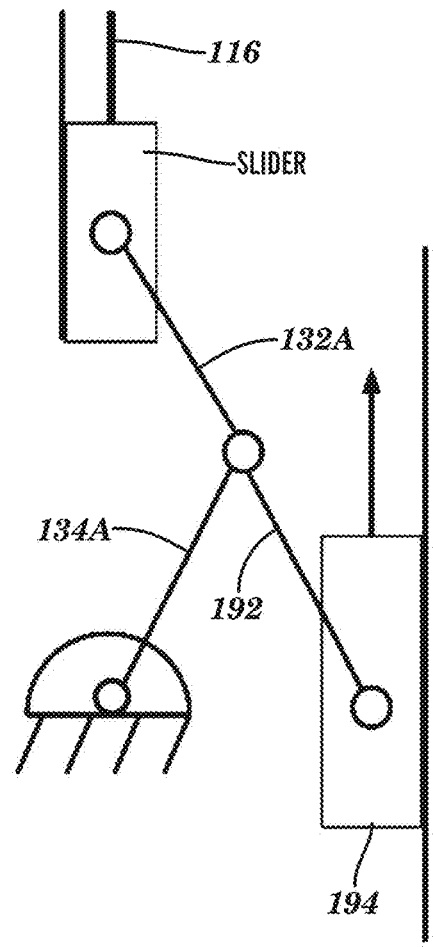
FIGS. 17A and 17B are diagrammatic views of a mechanism for transitioning a bi-stable coupling from the second position to the first position according to an embodiment of the invention.
Figure 17B:
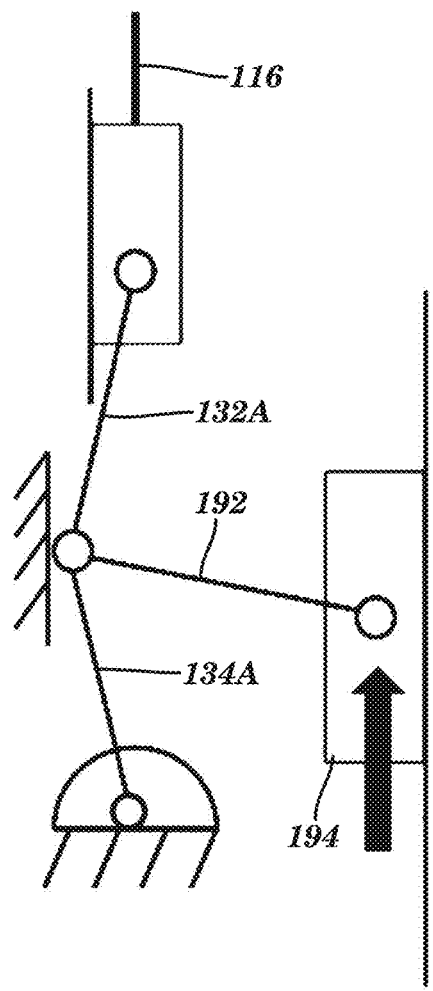

A reload mechanism can be provided that allows the user to reset the device to the drilling position and create additional holes. For example, FIGS. 17A and 17B illustrate one embodiment of a mechanism for transitioning the bi-stable coupling from the second, retracted position to the first, reloaded position. In this embodiment, a connecting link 192 connects a pusher 194 to the first bar 132A and the second bar 134A of the bi-stable coupling. FIG. 17A illustrates the mechanism in the retracted second position. When the pusher 194 is driven forward, the connecting link 192 forces the bi-stable links 132A, 134A past the second position and into the first position, as shown in FIG. 17B. In FIG. 17B, the device is reloaded to the drilling position and able to create additional holes. This embodiment may be implemented with respect to any of the bi-stable coupling configurations described herein.

FIGS. 18A-E illustrate an embodiment of a locking mechanism that can resist the bi-stable coupling spring forces in the absence of a force at the tool end. This enables the user to handle the bi-stable coupling 120 in the first position without physical effort. FIG. 18A is a partial diagrammatic view of the initial configuration of a locking mechanism with the bi-stable coupling 120 in the second position. The locking mechanism comprises locking bars 170A, 170B. FIG. 18B is a partial diagrammatic view of the bi-stable coupling 120 transitioning to the first position through some input force initiated by the user. In the process of transitioning, locking bars 170A and 170B open and allow drill bit 116 to pass through. FIG. 18C is a partial diagrammatic view of the locking mechanism holding the bi-stable coupling in the first position. Geometrical constraints in the locking mechanism prevent the bi-stable coupling 120 from retracting to the second position. FIG. 18D is a partial diagrammatic view of the locking mechanism passively disengaging during drilling of target material 172. FIG. 18E is a partial diagrammatic view of the locking mechanism allowing the bi-stable coupling 120 to return to the second position in the absence of a normal force at the drill bit 116. Although shown with respect to the bi-stable coupling 120 illustrated in FIGS. 15A-C, it is contemplated that this embodiment may be implemented in conjunction with any of the bi-stable couplings described herein.

FIGS. 19A-F illustrate another embodiment of a locking mechanism that can resist the bi-stable coupling spring forces in the absence of a force at the tool end. In this embodiment, a push ring 184 has features that extend beyond the housing which are allowed to travel along a predefined path (in this case, an L-shaped channel 188), as shown in FIG. 19A. Inside the housing 180, the push ring 184 can be used to move the pusher 186 and the bi-stable coupling into the first position. A return spring 190 prevents the push ring 184 from sliding to the bottom off the L-shaped channel 188, as shown in FIGS. 19B and 19C.

When the user applies a downward force to the push ring 184, this causes the bi-stable coupling to move to the first position, as shown in FIG. 19D, which illustrates the motions required to move push ring 184 into the first position such that the bi-stable coupling is locked into the first position. At the bottom of the L-shaped channel 188, the push ring 184 can be twisted counter-clockwise a small amount, mechanically constraining the push ring 184 and the bi-stable coupling from returning to the second position. The push ring 184 and the pusher 186 have mechanical mating features such that when the push ring 184 and the pusher 186 are in contact, they rotate together. When drilling is initiated, the push ring 184 and the pusher 186 rotate clockwise. Stored energy in the return spring 190 causes the push ring 184 and the pusher 186 to separate, whereby the push ring 184 is returned to the second position shown in FIG. 19A. If a normal force is applied to the drill bit 116 during this event, the bi-stable coupling will remain in the first position. When the normal force drops below a certain threshold, the bi-stable coupling will return to the second position. This embodiment may be implemented with respect to any of the bi-stable couplings described herein.

Manufacturing and Assembly

The majority of the parts (links, masses, threaded pins, adapter, and leader) can be purchased or professionally manufactured. The links and masses can be machined from brass to take advantage of the material's high density and increased centrifugal force during rotation. The adapter and leader can be machined from aluminum. Steel pins can be used for all revolute joints. The base members can be printed in a high resolution 3D printer. The casing and reloading system can be printed in a low resolution 3D printer. All other parts (steel pins, springs, screws, etc.) can be purchased off the shelf. Alternatively, the device could be made from plastic components for embodiments intended for single-use.

Evaluation

Figure 11A:
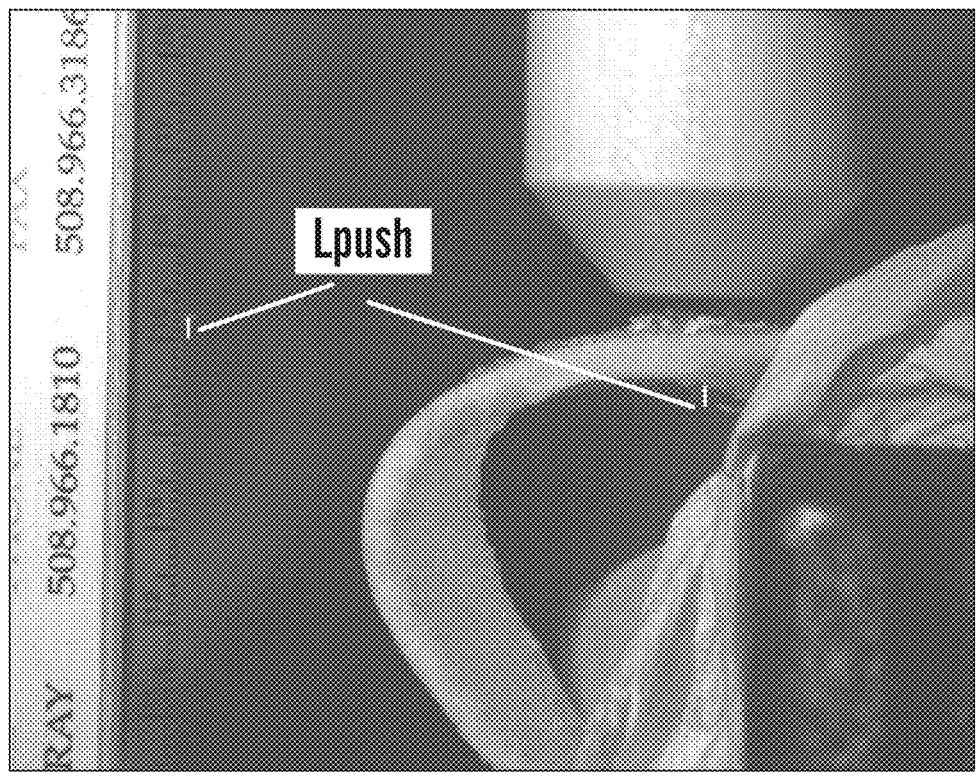
FIGS. 11A and 11B are diagrams showing the maximum bit penetration of a drill incorporating a bi-stable coupling according to an embodiment of the invention.
Figure 11B:
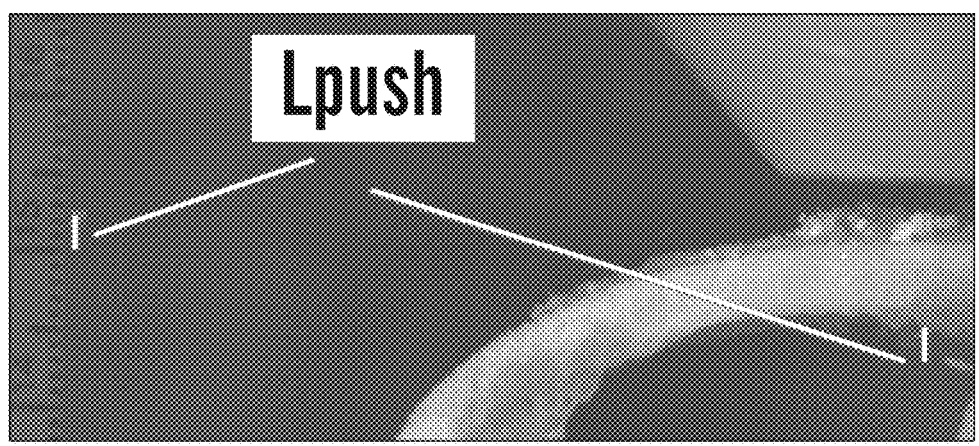

One embodiment of the device was evaluated using a high speed camera to capture the drilling process in real-time, especially after drill bit penetration. The high speed camera was focused on beef bones that were obtained from a local store. These bones, with cortical bone thickness measuring roughly 5 mm, provided a good approximation of the human skull for these experiments. FIGS. 11A and 11B include select frames from the high speed camera that show the maximum drill bit penetration (the max value of $L_{push}$) was approximately 2 mm. This was reasonably close to the estimated value calculated. The difference can be accounted for by manufacturing errors, friction forces, and small changes needed in the mechanical design.

The described embodiment of the present invention is directed to the design of a cranial drill with an automatic retraction coupling that avoids the risk of plunging after bit penetration through the bone. The design includes a bi-stable coupling whose transformation is triggered by centrifugal forces that pull a linkage open at the end of penetration when the reaction force on the drill bit reduces significantly. This design provides a safer drilling mechanism that can decrease the experience required for drilling holes on the skull without damaging the delicate brain tissue, enabling general surgeons to perform these procedures. Furthermore, the highly portable nature of the mechanism allows it to be used in all conditions including the emergency room or in the field for disaster relief and military operations. The bi-stable coupling works well in any orientation and is robust to external factors such as vibration.

The device according to the various embodiments of the invention can be used as an attachment to an existing drill or built into a sterile, standalone portable unit. The invention can support drill bit diameters from 2 mm (or less) to 7 mm (or more), covering the entire range of hole sizes needed for ICP monitoring, and could easily be fitted for larger diameter drill bits if needed. The device according to the invention can be used to penetrate the skull and safely remove itself without damaging brain tissue. The availability of this device could greatly increase the frequency of ICP monitoring for patients in many different settings, reducing the negative long-term effects caused by brain trauma.

The drilling device according to the invention provides an improvement over currently existing technology, and ensures that important medical procedures can be done safely and successfully. Possible procedures that could be done safely with drilling devices according to one or more embodiments of the present invention include: Skull penetration (for pressure monitor placement, for catheter insertion for drainage of cerebrospinal fluid, to administer medication directly to the area of need, to place electrodes for stimulating or recording brain activity, for abdominal and thoracic applications, for drilling/inserting screws into the sternum without injury to heart, for drilling/inserting screws into ribs without puncturing lungs, for penetrating vertebrae without injuring the spinal cord or its nerve roots, and for penetrating the pelvis or any long bones without injuring nerves or adjacent blood vessels and organs.

Our device can be attached to a battery powered drill. Multiple small drills bits can be incorporated so the clinician can make different sized holes when needed. The bi-stable coupling according to the invention can be used in other embodiments, for example, embodiments that involve pushing a needle or a tube through a layer of tissue. In this embodiment, the forces applied to the needle to penetrate the tissue can be used to hold the bi-stable coupling in the closed or first position. Upon penetrating the tissue layer, springs such as those shown in FIGS. 2 and 3 can be used to cause the coupling to transition to the open or second state to prevent the needle or tube from penetrating too deeply.

Other embodiments are within the scope and spirit of the invention. Features implementing functions may also be physically located at various positions, including being distributed such that portions of functions are implemented at different physical locations.

Further, while the description above refers to the invention, the description may include more than one invention.

REFERENCES

[1] D. Agamanolis, Neuropathology online course, Northeastern Ohio Universities College of Medicine (NEOUCOM) http://neuropathology.neoucom.edu/chapter4/chapter4aSubduralepidural.html.

[2] M. Gelabert-Gonzalez, V. Ginesta-Galan, R. Sernamito-Garcia, A. G. Allut, J. Bandin-Dieguez, R. M. Rumbo, "The Camino intracranial pressure device in clinical practice. Assessment in a 1000 cases," *ActaNeurochirurgica*, 148: pp. 435-441, 2005.

[3] D. Glauser, P. Flury, N. Villotte, C. W. Burckhardt, "Conception of a robot dedicated to neurosurgical operations," *Fifth International Conference on Advanced Robotics. Robots in Unstructured Environment*, vol. 1, pp. 899-904, 1991.

[4] J. D. Caird, K. A. Choudhari, "'Plunging' during burr hole craniostomy: a persistent problem amongst neurosurgeons in Britain and Ireland," *British Journal of Neurosurgery*, 17(6), pp. 509-512, 2003.

[5] N. Lynnerup, "Cranial thickness in relation to age, sex and general body build in a Danish forensic sample," *Forensic Science International*, vol. 117, pp. 45-51, 2001.

[7] M. Faul, L. Xu, M. M. Wald, V. G. Coronado, *Traumatic Brain Injury in the United States: Emergency Department Visits, Hospitalizations and Deaths 2002-2006*, Atlanta (Ga.): Centers for Disease Control and Prevention, National Center for Injury Prevention and Control, 2010.

[8] S.C. Stein, P. Georgoff, S. Meghan, K. L. Mirza, O. M. El Falaky, "Relationship of aggressive monitoring and treatment to improved outcomes in severe traumatic brain injury," *Journal of Neurosurgery*, 112, pp. 1105-1112, 2010.

[9] Integra Website, Products for Neurosurgeons, Cranial Access Kit, http://integralife.com/Neurosurgeon/Neurosurgeon-Product-Detail.aspx?Product=53&ProductName=Cranial%20Access%20Kit&ProductLineName=Cranial%20Access&ProductLineID=13

[10] "Acra-Cut Smart Drill," ACRA-CUT, 2003, http://www.acracut.com/images/pdf/smartdrill.pdf

[11] H. G. Reimels, et al., "Cranial Drill," U.S. Pat. No. 4,362,161, 1982.

[12] Y. Bar-Cohen, et al., "Ultrasonic Rotary-Hammer Drill," U.S. Pat. No. 7,740,088, 2010.

[13] M. D. Tsai, M. S. Hsieh, C. H. Tsai, "Bone drilling haptic interaction for orthopedic surgical simulator," *Computers in Biology and Medicine*, 37: 1709-1718, 2007.

The invention claimed is:

1. A drilling device comprising:
 a bi-stable coupling connecting a motor to a drill chuck, the drill chuck being adapted to rotate about a longitudinal axis as a result of a rotational force applied by the motor;
 wherein the bi-stable coupling having at least two positions;
 in a first position, the bi-stable coupling resists a reactive force applied along the longitudinal axis applied to the drill chuck; and
 in a second position, the bi-stable coupling does not resist a reactive force applied along the longitudinal axis applied to the drill chuck; and
 wherein the bi-stable coupling extends along the longitudinal axis having a first length while in the first position and a second, shorter length while in the second position.

2. The drilling device according to claim 1 wherein the bi-stable coupling includes at least one connecting arm pivotally mounted to the bi-stable coupling at a first end; the at least one connecting arm including a weight displaced from the first end, whereby the centrifugal force on the weight caused by the rotation of the bi-stable coupling causes the at least one connecting arm to extend outwardly from the longitudinal axis.

3. The drilling device according to claim 2 wherein the bi-stable coupling extends along the longitudinal axis having a first length and when centrifugal force is applied on the weight, the bi-stable coupling contracts to second length, shorter than the first length.

4. The drilling device according to claim 1 wherein the bi-stable coupling connects a rotational input to a drill chuck, the drill chuck being adapted to rotate about a longitudinal axis as a result of a rotational force applied by the motor; and at least one mass on the bi-stable coupling applies a centrifugal force causing the bi-stable coupling to change from the first position to the second position.

5. The drilling device according to claim 1 wherein the bi-stable coupling includes at least one spring that applies a force on the bi-stable coupling causing the bi-stable coupling to change from the first position to the second position.

6. A tool insertion device comprising:
 a bi-stable coupling connecting an input drive member to a tool
 wherein the bi-stable coupling having at least two positions;
 in a first position, the bi-stable coupling resists a reactive force applied along the longitudinal axis applied to the drill chuck; and
 in a second position, the bi-stable coupling collapses upon the removal of a reactive force applied to the tool along the longitudinal axis of the device; and wherein the bi-stable coupling extends along the longitudinal axis having a first length while in the first position and a second, shorter length while in the second position.

7. The tool insertion device according to claim 6 wherein the bi-stable coupling includes at least one connecting link pivotally mounted to the bi-stable coupling at the first and second end; and at least one drive member to apply a force radially to the longitudinal axis of the device that causes at least one connecting link to extend outwardly from the longitudinal axis.

8. The tool insertion device according to claim 7 wherein the bi-stable coupling extends along the longitudinal axis having a first length and when a force causes the connecting link to extend outward, the bi-stable coupling contracts to second length, shorter than the first length.

9. The tool insertion device according to claim 8 where in one embodiment the bi-stable coupling connects an input motor to a drill chuck, the drill chuck being adapted to rotate about a longitudinal axis as a result of a rotational force applied by the motor; and at least one mass on the at least one pivotally mounted link applies a centrifugal force changing the bi-stable coupling from its long state to its short state.

10. The tool insertion device according to claim 7 wherein the drive member includes at least one spring that applies a force on the at least one pivotally mounted link causing the bi-stable coupling to change from the longer state to the shorter state.

11. The tool insertion device according to claim 10, wherein the drive member further includes a spring along the longitudinal axis that increases or decreases a retraction force of the bi-stable coupling during transition from the first position to the second position.

12. The tool insertion device according to claim 11, further comprising:
    a locking mechanism configured to passively disengage during tool use.

13. The tool insertion device according to claim 10, further comprising:
    a locking mechanism configured to be engaged to resist the bi-stable coupling spring forces, thereby holding the bi-stable coupling in the first position.

14. A tool insertion device comprising:
    a bi-stable coupling connecting an input drive member to a tool, the bi-stable coupling comprising a first linkage and a second linkage;
    wherein the bi-stable coupling having at least two positions;
    in a first position, the bi-stable coupling resists a reactive force applied along the longitudinal axis applied to the drill chuck; and
    in a second position, the bi-stable coupling collapses upon the removal of a reactive force applied to the tool along the longitudinal axis of the device.

15. The tool insertion device according to claim 6, further comprising:
    a reloading mechanism configured to transition the bi-stable coupling from the second position to the first position.

16. The tool insertion device according to claim 14, wherein an angle between the first linkage and the second linkage is adjustable in the first position.

17. The tool insertion device according to claim 16, wherein an angle between the first linkage and the second linkage is adjustable in the second position.

* * * * *